(12) United States Patent
Kim et al.

(10) Patent No.: US 9,828,366 B2
(45) Date of Patent: Nov. 28, 2017

(54) BICYCLIC DERIVATIVES AND PHARMACEUTICAL COMPOSITION INCLUDING THE SAME

(71) Applicant: HANMI PHARM. CO., LTD., Hwaseong-si, Gyeonggi-do (KR)

(72) Inventors: Ji Sook Kim, Yongin-si (KR); Won Jeoung Kim, Suwon-si (KR); Wook Jang, Seoul (KR); Ji Young Song, Seoul (KR); Moon Sub Lee, Cheongju-si (KR); Nam Du Kim, Hwaseong-si (KR); Kwee Hyun Suh, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 15/308,435

(22) PCT Filed: May 8, 2015

(86) PCT No.: PCT/KR2015/004643
§ 371 (c)(1),
(2) Date: Nov. 2, 2016

(87) PCT Pub. No.: WO2015/174695
PCT Pub. Date: Nov. 19, 2015

(65) Prior Publication Data
US 2017/0066750 A1    Mar. 9, 2017

(30) Foreign Application Priority Data

May 13, 2014  (KR) .................. 10-2014-0057428
Jun. 30, 2014  (KR) .................. 10-2014-0081343

(51) Int. Cl.
| C07D 407/14 | (2006.01) |
| C07H 7/04 | (2006.01) |
| C07D 309/10 | (2006.01) |
| C07D 407/10 | (2006.01) |
| C07D 409/10 | (2006.01) |
| C07D 407/04 | (2006.01) |

(52) U.S. Cl.
CPC ......... *C07D 407/14* (2013.01); *C07D 309/10* (2013.01); *C07D 407/04* (2013.01); *C07D 407/10* (2013.01); *C07D 409/10* (2013.01); *C07H 7/04* (2013.01)

(58) Field of Classification Search
None
See application file for complete search history.

(56) References Cited

U.S. PATENT DOCUMENTS

| 5,712,279 | A | 1/1998 | Biller et al. |
| 5,712,396 | A | 1/1998 | Magnin et al. |
| 5,739,135 | A | 4/1998 | Biller et al. |
| 5,760,246 | A | 6/1998 | Biller et al. |
| 6,414,126 | B1 | 7/2002 | Ellsworth et al. |
| 6,627,611 | B2 | 9/2003 | Tomiyama et al. |
| 2006/0122126 | A1* | 6/2006 | Imamura ............... A61K 31/351 514/23 |

FOREIGN PATENT DOCUMENTS

| KR | 10-2002-0063876 A | 8/2002 |
| KR | 10-2006-0002818 A | 1/2006 |
| WO | 03/087093 A1 | 10/2003 |
| WO | 2006/082245 A1 | 8/2006 |

OTHER PUBLICATIONS

Adachi et al., Metabolism, vol. 49, No. 8, 2000, 990-995.*
R. H. Unger, et al., "Hyperglycaemia as an inducer as well as a consequence of impaired islet cell function and insulin resistance: implications for the management of diabetes", Diabetologia, 1985, pp. 119-121, vol. 28.
Luciano Rossetti, MD., et al., "Glucose Toxicity", Diabetes Care, Jun. 1990, pp. 610-630, vol. 13, No. 6.
Luciano Rossetti, et al., "Correction of Hyperglycemia with Phlorizin Normalizes Tissue Sensitivity to Insulin on Diabetic Rats", J. Clin. Invest., May 1987, pp. 1510-1515, vol. 79.
P. T. Clayton, et al., "Familial Giant Cell Hepatitis Associated with Synthesis of 3β,7α-Dihydroxy- and 3β,7α,12α-Trihydroxy-5-Cholenoic Acids", J. Clin. Invest., Apr. 1987, pp. 1031-1038, vol. 79.
B. A. Adkins, et al., "Importance of the Route of Intravenous Glucose Delivery to Hepatic Glucose Balance in the Conscious Dog", J. Clin. Invest., Feb. 1987, pp. 557-565, vol. 79.
Eric A. Owens, et al., "Near-Infrared Illumination of Native Tissues for Image-Guided Surgery", Journal of Medicinal Chemistry, 1999, pp. 5311-5323, vol. 42.
Kenji Arakawa, et al., "Improved diabetic syndrome in C57BL/KsJ-db/db mice by oral administration of the Na⁺-glucose cotransporter inhibitor T-1095", British Journal of Pharmacology, 2001, pp. 578-586, vol. 132.
Adolfo Andrade-Cetto, et al.,"Hypoglycemic effect of *Cecropia obtusifolia* on streptozotocin diabetic rats", Journal of Ethnopharmacology, 2001, pp. 145-149, vol. 78.
International Searching Authority, International Search Report for PCT/KR2015/004643 dated Aug. 21, 2015 [PCT/ISA/210].
International Searching Authority, Written Opinion for PCT/KR2015/004643 dated Aug. 21, 2015 [PCT/ISA/237].

* cited by examiner

*Primary Examiner* — Traviss C McIntosh, III
(74) *Attorney, Agent, or Firm* — Sughrue Mion, PLLC

(57) ABSTRACT

The present invention relates to a novel bicyclic derivative that has an inhibitory activity against sodium-glucose linked transporters (SGLTs) present in the intestines and kidneys, or a pharmaceutically acceptable salt, isomer, hydrate or solvate thereof, and a pharmaceutical composition including the same as an active ingredient, which effectively inhibit the SGLT activity, and thus can be used as a therapeutic agent to treat diseases caused by hyperglycemia, such as diabetes including insulin-dependent diabetes (type I diabetes mellitus) and non-insulin-dependent diabetes (type II diabetes mellitus), diabetic complications, and obesity.

13 Claims, 1 Drawing Sheet

BICYCLIC DERIVATIVES AND PHARMACEUTICAL COMPOSITION INCLUDING THE SAME

CROSS REFERENCE TO RELATED APPLICATIONS

This application is a National Stage of International Application No. PCT/KR2015/004643, filed on May 8, 2015, which claims priority from Korean Patent Application Nos. 10-2014-0057428, filed on May 13, 2014, and 10-2014-0081343, filed on Jun. 30, 2014, the contents of all of which are incorporated herein by reference in their entirety.

FIELD OF THE INVENTION

The present invention relates to a novel bicyclic derivative that has an inhibitory activity against sodium-glucose linked transporters (SGLTs) present in the intestines and kidneys, or a pharmaceutically acceptable salt, isomer, hydrate or solvate thereof, and a pharmaceutical composition including the same as an active ingredient.

BACKGROUND OF THE INVENTION

Owing to the Western dietary lifestyle and chronic lack of exercise, approximately three hundred million people around the world suffer from type II diabetes mellitus, which is characterized by hyperglycemia resulting from excessive hepatic glucose production and peripheral insulin resistance, and the number of diabetic patients is increasing. Dietary and exercise therapies are essential for treatment of diabetes, but insulin or several oral antidiabetic agents are further used when these therapies do not sufficiently control the patients' symptoms.

In recent years, a biguanide compound, a sulfonylurea compound, an insulin resistance modifier, and an α-glucosidase inhibitor have been used as antidiabetic agents, but these antidiabetic agents have several side effects. For example, the biguanide compound causes lactic acidosis, the sulfonylurea compound causes severe hypoglycemia, the insulin resistance modifier causes swelling and heart failure, and the α-glucosidase inhibitor causes abdominal distention and diarrhea. Under such situations, there is a need for development of novel drugs that are able to treat diabetes without causing the above-described side effects.

In recent years, the glucose toxicity theory in which hyperglycemia is associated with the onset of diabetes, and progressive disorders such as diabetic complications has been reported. That is, chronic hyperglycemia causes a decrease in insulin secretion and a reduction in insulin sensitivity, resulting in self-worsening diabetes due to an increase in blood glucose concentration [see *Diabetologia* (1985) 28, p. 119; and *Diabetes Care* (1990) 13, p. 610]. Therefore, hyperglycemia may be treated to stop the above-described self-worsening cycle, thereby treating or preventing diabetes.

As one method of treating hyperglycemia, a method of directly secreting an excessive amount of glucose in urine so that the blood glucose concentration decreases to a normal range may be contemplated. For example, when the sodium-glucose linked transporters (SGLTs) present in proximal convoluted tubules of the kidney are inhibited, the glucose reuptake in the kidney is inhibited, and thus, the secretion of glucose in the urine is stimulated, resulting in a decrease in the blood glucose concentration. In fact, it was confirmed that, when phlorizin having an SGLT inhibitory activity is subcutaneously administered continuously in a diabetic animal model, hyperglycemia may return to a normal state, and a blood glucose level may be maintained for a long period of time in a normal range, resulting in an increase in insulin secretion and improvement of insulin tolerance [see *Journal of Clinical Investigation* (1987) 79, p. 1510; ibid. p. 1037; ibid. p. 561].

Also, while a diabetic animal model is treated with the SGLT inhibitor for a long period of time, the SGLT inhibitor does not cause side effects in the kidney of the animal and a response of increased insulin secretion and improved insulin sensitivity is exhibited without causing any imbalance in the level of electrolytes in the blood. As a result, the onset and progression of diabetic nephropathy and neuropathy are prevented [see *Journal of Medicinal Chemistry* (1999) 42, p 5311; and *British Journal of Pharmacology* (2001) 132, p. 578].

Accordingly, it can be expected from the above-described results that the SGLT inhibitor increases insulin secretion and improves insulin tolerance by reducing a blood glucose level in diabetic patients, and also prevents the onset and progression of diabetes and diabetic complications.

SUMMARY OF THE INVENTION

Therefore, it is an aspect of the present invention to provide a novel bicyclic derivative that has an inhibitory activity against sodium-glucose linked transporters (SGLTs) present in the intestines and kidneys, or a pharmaceutically acceptable salt, isomer, hydrate or solvate thereof.

Also, it is another aspect of the present invention to provide a pharmaceutical composition including the compound as an active ingredient.

In accordance with an aspect of the present invention, there is provided a bicyclic derivative represented by the following Formula 1, or a pharmaceutically acceptable salt, isomer, hydrate or solvate thereof:

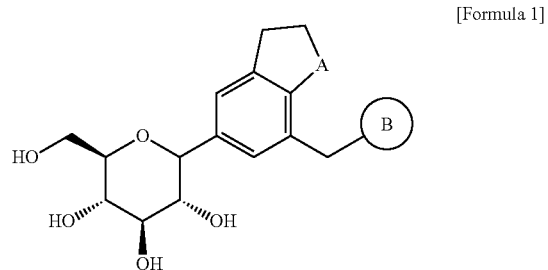

[Formula 1]

wherein
A is —O— or —CH$_2$—;
the ring B is selected from the group consisting of the following Structural Formulae (i), (ii) and (iii):

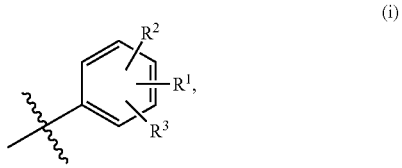

(i)

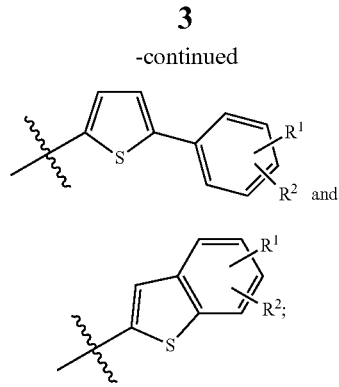

R[1], R[2], and R[3] each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 5 fluoro groups, $C_{1-4}$ alkyl, $C_{3-6}$ cycloalkyl, $C_{1-8}$ alkoxy, 3- to 6-membered heterocycloalkyloxy, or $C_{1-3}$ alkylsulfonyl groups, wherein the $C_{1-8}$ alkoxy may be substituted with one to two $C_{1-8}$ alkoxy or $C_{3-6}$ cycloalkyloxy groups;

R[1] and R[2] substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—R[4])—, and unreplaced methylene groups may be each independently substituted with 1 to 4 halogens or methyl groups;

R[4] is H or benzyl; and the heterocycloalkyl includes at least one heteroatom selected from the group consisting of O, N, and S.

In accordance with another aspect of the present invention, there is provided a pharmaceutical composition including the bicyclic derivative represented by Formula 1, or the pharmaceutically acceptable salt, isomer, hydrate or solvate thereof as an active ingredient.

The present invention also provide a use of the bicyclic derivative of Formula 1, or the pharmaceutically acceptable salt, isomer, hydrate or solvate thereof for the manufacture of a medicament for preventing or treating a disease or condition mediated by hyperglycemia.

The present invention also provide a method of preventing or treating a disease or condition mediated by hyperglycemia in a mammal, which includes administering the bicyclic derivative of Formula 1, or the pharmaceutically acceptable salt, isomer, hydrate or solvate thereof to the mammal.

The bicyclic derivative of Formula 1 according to one exemplary embodiment of the present invention, or the pharmaceutically acceptable salt, isomer, hydrate or solvate thereof effectively inhibits the SGLT activity, and thus can be used as a therapeutic agent to treat diseases caused by hyperglycemia, such as diabetes including insulin-dependent diabetes (type I diabetes mellitus) and non-insulin-dependent diabetes (type II diabetes mellitus), diabetic complications, and obesity.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
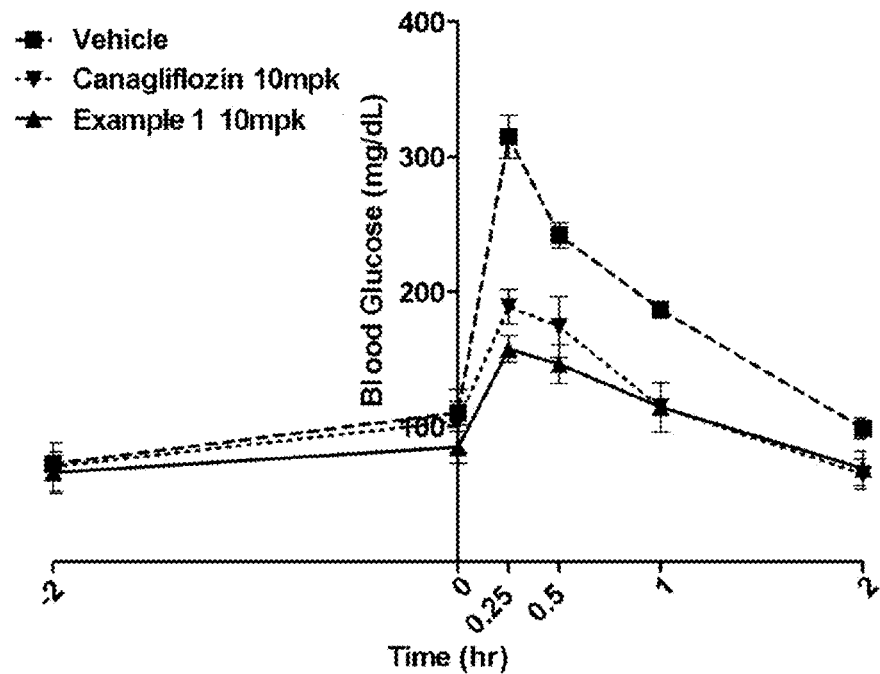
FIG. 1: a graph illustrating blood glucose concentrations depending on time after the compound of Example 1, 5% 1-methyl-2-pyrrolidinone as a vehicle, a mixed solution of 20% PEG and 75% 20 mM sodium diphophate, and canagliflozin as a control are orally administered to mice.

Hereinafter, the present invention will be described in further detail.

The term "halogen" or "halo" used herein refers to fluorine, chlorine, bromine, or iodine, or a fluoro group, chloro group, bromo group, or iodo group.

The term "alkyl" used herein refers to a linear or branched saturated $C_1$ to $C_8$ hydrocarbon radical chain. Specifically, the alkyl may include methyl, ethyl, n-propyl, isopropyl, n-butyl, isobutyl, t-butyl, n-pentyl, isopentyl, hexyl, heptyl, octyl, and the like, but is not limited thereto.

The term "cycloalkyl" used herein refers to cyclopropyl, cyclobutyl, cyclopentyl, cyclohexyl, and the like, but is not limited thereto.

Unless specifically stated otherwise, the term "heterocycloalkyl" used herein refers to a heterocycloalkyl containing at least one heteroatom selected from O, N and S in a cycloalkyl ring. The heterocycloalkyl may include oxetane, tetrahydrofuran, dioxolane, dioxane, pyrrolidine, or piperidine, but is not limited thereto.

One exemplary embodiment of the present invention provides a bicyclic derivative represented by the following Formula 1, or a pharmaceutically acceptable salt, isomer, hydrate or solvate thereof:

[Formula 1]

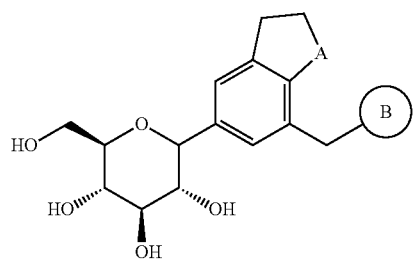

wherein
A is —O— or —CH$_2$—;
the ring B is selected from the group consisting of the following Structural Formulae (i), (ii) and (iii):

(i)

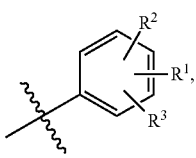

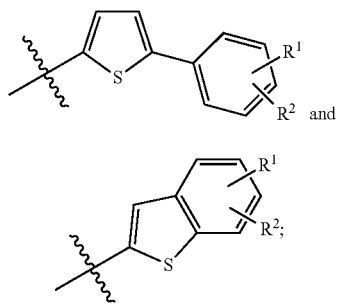

$R^1$, $R^2$, and $R^3$ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 5 fluoro groups, $C_{1-4}$ alkyl, $C_{3-6}$ cycloalkyl, $C_{1-8}$ alkoxy, 3- to 6-membered heterocycloalkyloxy, or $C_{1-3}$ alkylsulfonyl groups, wherein the $C_{1-8}$ alkoxy may be substituted with one to two $C_{1-8}$ alkoxy or $C_{3-6}$ cycloalkyloxy groups;

$R^1$ and $R^2$ substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—$R^4$)—, and unreplaced methylene groups may be each independently substituted with 1 to 4 halogens or methyl groups;

$R^4$ is H or benzyl; and the heterocycloalkyl includes at least one heteroatom selected from the group consisting of O, N, and S.

In a preferred embodiment of the compound of Formula 1,

A is —O— or —CH$_2$—;

the ring B is represented by Structural Formula (i);

$R^1$, $R^2$, and $R^3$ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 3 fluoro groups, $C_{1-4}$ alkyl, $C_{3-6}$ cycloalkyl, $C_{1-8}$ alkoxy, 3- to 6-membered heterocycloalkyloxy, or methylsulfonyl groups, wherein the $C_{1-8}$ alkoxy may be substituted with one to two $C_{1-8}$ alkoxy or $C_{3-6}$ cycloalkyloxy groups;

$R^1$ and $R^2$ substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—$R^4$)—, and unreplaced methylene groups may be each independently substituted with one to two fluoro groups or methyl groups;

$R^4$ is H or benzyl; and the heterocycloalkyl includes at least one heteroatom selected from the group consisting of O, N, and S.

In a preferred embodiment of the compound of Formula 1,

A is —O— or —CH$_2$—;

the ring B is represented by Structural Formula (ii) or (iii); and $R^1$ and $R^2$ each independently are H, halogen, hydroxy, or $C_{1-8}$ alkyl.

In a preferred embodiment of the compound of Formula 1,

A is —O—;

the ring B is represented by Structural Formula (i);

$R^1$, $R^2$, and $R^3$ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 3 fluoro groups, $C_{1-4}$ alkyl, $C_{3-6}$ cycloalkyl, $C_{1-8}$ alkoxy, 3- to 6-membered heterocycloalkyloxy, or methylsulfonyl groups, wherein the $C_{1-8}$ alkoxy may be substituted with one to two $C_{1-8}$ alkoxy or $C_{3-6}$ cycloalkyloxy groups;

$R^1$ and $R^2$ substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—$R^4$)—, and unreplaced methylene groups may be each independently substituted with one to two fluoro groups or methyl groups;

$R^4$ is H or benzyl; and the heterocycloalkyl includes at least one heteroatom selected from the group consisting of O, N, and S.

In a preferred embodiment of the compound of Formula 1,

A is —O—;

the ring B is represented by Structural Formula (ii) or (iii);

$R^1$ and $R^2$ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 3 fluoro groups, $C_{1-4}$ alkyl, $C_{3-6}$ cycloalkyl, $C_{1-8}$ alkoxy, 3- to 6-membered heterocycloalkyloxy, or methylsulfonyl groups, wherein the $C_{1-8}$ alkoxy may be substituted with one to two $C_{1-8}$ alkoxy or $C_{3-6}$ cycloalkyloxy groups;

$R^1$ and $R^2$ substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—$R^4$)—, and unreplaced methylene groups may be each independently substituted with one to two fluoro groups or methyl groups;

$R^4$ is H or benzyl; and the heterocycloalkyl includes at least one heteroatom selected from the group consisting of O, N, and S.

In a preferred embodiment of the compound of Formula 1,

A is —CH$_2$—;

the ring B is represented by Structural Formula (i), (ii) or (iii);

$R^1$, $R^2$, and $R^3$ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{3-6}$ cycloalkyl, $C_{1-8}$ alkoxy, and $C_{3-6}$ cycloalkyloxy may be each independently substituted with 1 to 5 fluoro groups, $C_{1-8}$ alkyl, $C_{3-6}$ cycloalkyl, or $C_{1-8}$ alkoxy groups; and $R^1$ and $R^2$ substituted at two adjacent carbon atoms may be joined together to form $C_{3-5}$ alkylene bridge, where one to two methylene groups in the $C_{3-5}$ alkylene bridge may be replaced with an oxygen atom, and methylene groups which are not replaced with oxygen atoms may be each independently substituted with one to two fluoro or methyl groups.

In a more preferred embodiment of the compound of Formula 1,

A is —CH$_2$—;

the ring B is represented by Structural Formula (i);

R$^1$, R$^2$, and R$^3$ each independently are H, halogen, hydroxy, C$_{1-8}$ alkyl, C$_{2-7}$ alkynyl, C$_{3-6}$ cycloalkyl, C$_{1-8}$ alkoxy, or C$_{3-6}$ cycloalkyloxy, wherein the C$_{1-8}$ alkyl, C$_{3-6}$ cycloalkyl, C$_{1-8}$ alkoxy, and C$_{3-6}$ cycloalkyloxy may be each independently substituted with 1 to 3 fluoro groups, C$_{1-8}$ alkyl, C$_{3-6}$ cycloalkyl, or C$_{1-8}$ alkoxy groups; and R$^1$ and R$^2$ substituted at two adjacent carbon atoms may be joined together to form C$_{3-5}$ alkylene bridge, where one to two methylene groups in the C$_{3-5}$ alkylene bridge may be replaced with an oxygen atom, and methylene groups which are not replaced with oxygen atoms may be each independently substituted with one to two fluoro or methyl groups.

In a much more preferred embodiment of the compound of Formula 1,

A is —CH$_2$—;

the ring B is represented Structural Formula (i); and

R$^1$, R$^2$, and R$^3$ each independently are H, a fluoro group, a chloro group, a hydroxy, C$_{1-6}$ alkyl, C$_{3-6}$ cycloalkyl, or C$_{1-6}$ alkoxy, wherein the C$_{1-6}$ alkyl and C$_{1-6}$ alkoxy may be each independently substituted with 1 to 3 C$_{1-6}$ alkyl or fluoro groups; and R$^1$ and R$^2$ substituted at two adjacent carbon atoms may be joined together to form —O—(R$^4$)$_n$—O— (wherein n is 1 or 2, and R$^4$ each independently is —CH$_2$—, —CH(CH$_3$)—, or —C(CH$_3$)$_2$—).

In a preferred embodiment of the compound of Formula 1,

A is —CH$_2$—;

the ring B is represented by Structural Formula (ii) or (iii);

R$^1$ and R$^2$ each independently are H, halogen, hydroxy, C$_{1-8}$ alkyl, C$_{2-7}$ alkenyl, C$_{2-7}$ alkynyl, C$_{3-6}$ cycloalkyl, C$_{1-8}$ alkoxy, or C$_{3-6}$ cycloalkyloxy, wherein the C$_{1-8}$ alkyl, C$_{3-6}$ cycloalkyl, C$_{1-8}$ alkoxy, and C$_{3-6}$ cycloalkyloxy may be each independently substituted with 1 to 5 fluoro groups, C$_{1-8}$ alkyl, C$_{3-6}$ cycloalkyl, or C$_{1-8}$ alkoxy groups; and R$^1$ and R$^2$ substituted at two adjacent carbon atoms may be joined together to form C$_{3-5}$ alkylene bridge, where one to two methylene groups in the C$_{3-5}$ alkylene bridge may be replaced with an oxygen atom, and methylene groups which are not replaced with oxygen atoms may be each independently substituted with one to two fluoro or methyl groups.

Specific examples of the bicyclic derivative of Formula 1 according to one exemplary embodiment of the present invention are described below, or a pharmaceutically acceptable salt, isomer, hydrate or solvate thereof may also be used:

1) (2S,3R,4R,5S,6R)-2-(7-(4-ethoxybenzyl)-2,3-dihydrobenzofuran-5-yl)-6-hydroxymethyl-tetrahydro-2H-pyran-3,4,5-triol;

2) (2S,3R,4R,5S,6R)-2-(7-(4-ethylbenzyl)-2,3-dihydrobenzofuran-5-yl)-6-hydroxymethyl-tetrahydro-2H-pyran-3,4,5-triol;

3) (2R,3S,4R,5R,6S)-2-hydroxymethyl-6-(7-(4-n-propylbenzyl)-2,3-dihydrobenzofuran-5-yl)-tetrahydro-2H-pyran-3,4,5-triol;

4) (2R,3S,4R,5R,6S)-2-hydroxymethyl-6-(7-(4-trifluoromethylbenzyl)-2,3-dihydrobenzofuran-5-yl)tetrahydro-2H-pyran-3,4,5-triol;

5) (2R,3S,4R,5R,6S)-2-hydroxymethyl-6-(7-(4-trifluoromethoxybenzyl)-2,3-dihydrobenzofuran-5-yl)tetrahydro-2H-pyran-3,4,5-triol;

6) (2S,3R,4R,5S,6R)-2-(7-(4-fluorobenzyl)-2,3-dihydrobenzofuran-5-yl)-6-(hydroxymethyl)tetrahydro-2H-pyran-3,4,5-triol;

7) (2S,3R,4R,5S,6R)-2-(7-((2,3-dihydrobenzo[b][1,4]dioxin-6-yl)methyl)-2,3-dihydrobenzofuran-5-yl)-6-(hydroxymethyl)tetrahydro-2H-pyran-3,4,5-triol;

8) (2S,3R,4R,5S,6R)-2-(7-(4-(cyclopropylmethoxy)benzyl)-2,3-dihydrobenzofuran-5-yl)-6-(hydroxymethyl)tetrahydro-2H-pyran-3,4,5-triol;

9) (2S,3R,4R,5S,6R)-2-(7-(4-ethoxy-3-fluorobenzyl)-2,3-dihydrobenzofuran-5-yl)-6-(hydroxymethyl)tetrahydro-2H-pyran-3,4,5-triol;

10) (2S,3R,4R,5S,6R)-2-(7-(4-ethoxy-2-fluorobenzyl)-2,3-dihydrobenzofuran-5-yl)-6-(hydroxymethyl)tetrahydro-2H-pyran-3,4,5-triol;

11) (2S,3R,4R,5S,6R)-2-(7-(4-hydroxybenzyl)-2,3-dihydrobenzofuran-5-yl)-6-(hydroxymethyl)tetrahydro-2H-pyran-3,4,5-triol;

12) (2S,3S,4R,5R,6S)-2-(hydroxymethyl)-6-(7-(4-(3-(methylsulfonyl)propoxy)benzyl)-2,3-dihydrofuran-5-yl)tetrahydro-2H-pyran-3,4,5-triol;

13) (2S,3R,4R,5S,6R)-2-(7-(4-ethoxybenzyl)-2,3-dihydro-1H-inden-5-yl)-6-(hydroxymethyl)tetrahydro-2H-pyran-3,4,5-triol;

14) (2R,3S,4R,5R,6S)-2-(hydroxymethyl)-6-(7-(4-methoxybenzyl)-2,3-dihydro-1H-inden-5-yl)tetrahydro-2H-pyran-3,4,5-triol;

15) (2R,3S,4R,5R,6S)-2-(hydroxymethyl)-6-(7-(4-methylbenzyl)-2,3-dihydro-1H-inden-5-yl)tetrahydro-2H-pyran-3,4,5-triol;

16) (2S,3R,4R,5S,6R)-2-(7-(4-ethylbenzyl)-2,3-dihydro-1H-inden-5-yl)-6-(hydroxymethyl)tetrahydro-2H-pyran-3,4,5-triol;

17) (2R,3S,4R,5R,6S)-2-(hydroxymethyl)-6-(7-(4-propylbenzyl)-2,3-dihydro-1H-inden-5-yl)tetrahydro-2H-pyran-3,4,5-triol;

18) (2R,3S,4R,5R,6S)-2-(hydroxymethyl)-6-(7-(4-isopropylbenzyl)-2,3-dihydro-1H-inden-5-yl)tetrahydro-2H-pyran-3,4,5-triol;

19) (2S,3R,4R,5S,6R)-2-(7-benzyl-2,3-dihydro-1H-inden-5-yl)-6-(hydroxymethyl)tetrahydro-2H-pyran-3,4,5-triol;

20) (2S,3R,4R,5S,6R)-2-(7-(4-ethoxy-3-fluorobenzyl)-2,3-dihydro-1H-inden-5-yl)-6-(hydroxymethyl)tetrahydro-2H-pyran-3,4,5-triol;

21) (2S,3R,4R,5S,6R)-2-(7-(4-ethoxy-2-fluorobenzyl)-2,3-dihydro-1H-inden-5-yl)-6-(hydroxymethyl)tetrahydro-2H-pyran-3,4,5-triol;

22) (2R,3S,4R,5R,6S)-2-(hydroxymethyl)-6-(7-(4-(trifluoromethoxy)benzyl)-2,3-dihydro-1H-inden-5-yl)tetrahydro-2H-pyran-3,4,5-triol;

23) (2S,3R,4R,5S,6R)-2-(7-(4-ethoxy-2,6-dimethylbenzyl)-2,3-dihydro-1H-inden-5-yl)-6-(hydroxymethyl)tetrahydro-2H-pyran-3,4,5-triol;

24) (2R,3S,4R,5R,6S)-2-(hydroxymethyl)-6-(7-(4-(trifluoromethyl)benzyl)-2,3-dihydro-1H-inden-5-yl)tetrahydro-2H-pyran-3,4,5-triol;

25) (2S,3R,4R,5S,6R)-2-(7-(3-fluoro-4-methylbenzyl)-2,3-dihydro-1H-inden-5-yl)-6-(hydroxymethyl)tetrahydro-2H-pyran-3,4,5-triol;

26) (2S,3R,4R,5S,6R)-2-(7-(2-fluoro-4-methylbenzyl)-2,3-dihydro-1H-inden-5-yl)-6-(hydroxymethyl)tetrahydro-2H-pyran-3,4,5-triol;

27) (2S,3R,4R,5S,6R)-2-(7-(3,4-(dimethoxybenzyl)2,3-dihydro-1H-inden-5-yl)-6-(hydroxymethyl)tetrahydro-2H-pyran-3,4,5-triol;

28) (2S,3R,4R,5S,6R)-2-(7-(4-ethyl-3-fluorobenzyl)-2,3-dihydro-1H-inden-5-yl)-6-(hydroxymethyl)tetrahydro-2H-pyran-3,4,5-triol;
29) (2S,3R,4R,5S,6R)-2-(7-(benzo[d][1,3]dioxol-5-ylmethyl)-2,3-dihydro-1H-inden-5-yl)-6-(hydroxymethyl) tetrahydro-2H-pyran-3,4,5-triol;
30) (2S,3R,4R,5S,6R)-2-(7-((2,3-dihydrobenzo[1,4]dioxin-6-yl)methyl)-2,3-dihydro-1H-inden-5-yl)-6-(hydroxymethyl)tetrahydro-2H-pyran-3,4,5-triol;
31) (2S,3R,4R,5S,6R)-2-(7-(4-(tert-butyl)benzyl)-2,3-dihydro-1H-inden-5-yl)-6-(hydroxymethyl)tetrahydro-2H-pyran-3,4,5-triol;
32) (2S,3R,4R,5S,6R)-2-(7-(3,4-dimethylbenzyl)-2,3-dihydro-1H-inden-5-yl)-6-(hydroxymethyl)tetrahydro-2H-pyran-3,4,5-triol;
33) (2R,3S,4R,5R,6S)-2-(hydroxymethyl)-6-(7-(3-methylbenzyl)-2,3-dihydro-1H-inden-5-yl)tetrahydro-2H-pyran-3,4,5-triol;
34) (2R,3S,4R,5R,6S)-2-(hydroxymethyl)-6-(7-(4-(2,2,2-trifluoroethoxy)benzyl)-2,3-dihydro-1H-inden-5-yl)tetrahydro-2H-pyran-3,4,5-triol;
35) (2S,3R,4R,5S,6R)-2-(7-((2,2-dimethylbenzo[d][1,3]dioxol-5-yl)methyl)-2,3-dihydro-1H-inden-5-yl)-6-(hydroxymethyl)tetrahydro-2H-pyran-3,4,5-triol;
36) (2S,3R,4R,5S,6R)-2-(7-((5-(4-fluorophenyl)thiophen-2-yl)methyl)-2,3-dihydro-1H-inden-5-yl)-6-(hydroxymethyl)tetrahydro-2H-pyran-3,4,5-triol;
37) (2S,3R,4R,5S,6R)-2-(7-(benzo[b]thiophen-2-ylmethyl)-2,3-dihydro-1H-inden-5-yl)-6-(hydroxymethyl)tetrahydro-2H-pyran-3,4,5-triol;
38) (2S,3R,4R,5S,6R)-2-(7-(4-cyclopropylbenzyl)-2,3-dihydro-1H-inden-5-yl)-6-(hydroxymethyl)tetrahydro-2H-pyran-3,4,5-triol;
39) (2S,3R,4R,5S,6R)-2-(7-(4-cyclopropyl-2-fluorobenzyl)-2,3-dihydro-1H-inden-5-yl)-6-(hydroxymethyl)tetrahydro-2H-pyran-3,4,5-triol; and
40) (2S,3R,4R,5S,6R)-2-(7-(4-chlorobenzyl)-2,3-dihydro-1H-inden-5-yl)-6-(hydroxymethyl)tetrahydro-2H-pyran-3,4,5-triol.

The bicyclic derivative of Formula 1, or the pharmaceutically acceptable salt, isomer, hydrate or solvate thereof are all included in the scope of the compound according to one exemplary embodiment of the present invention.

Such a pharmaceutically acceptable salt may be used when the pharmaceutically acceptable salt is formed from an inorganic acid or an organic acid. For example, the pharmaceutically acceptable salt includes a salt of an inorganic acid such as hydrochloric acid, sulfuric acid, nitric acid, phosphoric acid, perchloric acid, or bromic acid; a salt of an organic acid such as formic acid, acetic acid, propionic acid, oxalic acid, succinic acid, benzoic acid, citric acid, maleic acid, malonic acid, malic acid, tartaric acid, gluconic acid, lactic acid, gastric acid, fumaric acid, lactobionic acid, salicylic acid, phthalic acid, embonic acid, aspartic acid, glutamic acid, or acetylsalicylic acid (aspirin); a salt of an amino acid such as glycine, alanine, valine, isoleucine, serine, cysteine, cystine, asparagine, glutamine, lysine, arginine, tyrosine, or proline; salts of sulfonic acids such as methanesulfonic acid, ethanesulfonic acid, benzenesulfonic acid, or toluenesulfonic acid; an alkali metal salt such as sodium or potassium; or an ammonium ionic salt.

Also, the pharmaceutically acceptable salt may include an organic base addition salt formed from an organic base such as tris(hydroxymethyl)methylamine, dicyclohexylamine, etc.

Such a pharmaceutically acceptable salt of the bicyclic derivative of Formula 1 may be prepared using conventional methods known in the art. For example, the pharmaceutically acceptable salt may be prepared by dissolving the bicyclic derivative of Formula 1 in a water-miscible solvent such as methanol, ethanol, acetone, or 1,4-dioxane, adding a free acid or base to the resulting mixture, and crystallizing the mixture.

Further, the compounds of the present invention may have a chiral carbon center, and thus they may be present in the form of an R or S isomer, a racemic compound, an individual enantiomer or a mixture, an individual diastereomer or a mixture, and all these stereoisomers and a mixture thereof are included in the scope of the present invention.

Additionally, the compounds of the present invention may also include a hydrate or solvate of the bicyclic derivative represented by Formula 1. The hydrate or solvate may be prepared using a known method, and they may be non-toxic and water-soluble, and in particular, they may be preferably water or a hydrate or solvate having 1-5 molecules of alcoholic solvent (especially ethanol, etc.) bound thereto.

The bicyclic derivative of Formula 1 according to one exemplary embodiment of the present invention, or the pharmaceutically acceptable salt, isomer, hydrate or solvate thereof may be effectively used to prevent or treat a disease or condition mediated by hyperglycemia by inhibiting the SGLT activity.

Therefore, the present invention provides a pharmaceutical composition including the bicyclic derivative of Formula 1, or the pharmaceutically acceptable salt, isomer, hydrate or solvate thereof as an active ingredient.

The pharmaceutical composition according to one exemplary embodiment of the present invention may be used to inhibit the SGLT activity, thereby preventing or treating the hyperglycemia-mediated disease or condition such as diabetes, a diabetes-related disease, and diabetic complications.

The diabetes includes insulin-dependent diabetes (type I diabetes mellitus), and non-insulin-dependent diabetes (type II diabetes mellitus), and also includes other types of diabetes developed by certain causes.

Examples of the diabetes-related disease may include obesity, hyperinsulinemia, an impaired glucose metabolism, hyperlipidemia, hypercholesteremia, hypertriglyceridemia, an impaired lipid metabolism, hypertension, congestive heart failure, edema, hyperuricemia, gout, etc., but are not limited thereto.

The diabetic complications include both acute complications and chronic complications.

The acute complications may include hyperglycemia (ketoacidosis, etc.), diabetic infection symptoms (skin infection, soft tissue infection, biliary tract infection, respiratory tract infection, urinary tract infection, etc.), etc.

The chronic complications may include diabetic microangiopathy (nephrosis, renal failure, retinosis, etc.), diabetic arterial sclerosis (atherosclerosis, myocardial infarction, cerebral infarction, peripheral arterial occlusion, etc.), diabetic nerve disorders (sensory nerve disorders, motor nerve disorders, autonomic nerve disorders, etc.), diabetic ulcers, etc.

The main diabetic complications may include diabetic retinosis, diabetic renal failure, and diabetic nerve disorder, but are not limited thereto.

In addition to the SGLT activity inhibitors, the compound according to one exemplary embodiment of the present invention may also be used together with at least one therapeutic agent selected from the group consisting of antidiabetic agents having different mechanisms, antidiabetic complication agents, and antihyperlipidemic agents, antihypertensive agents.

The compound according to one exemplary embodiment of the present invention may be expected to have a synergetic effect on treatment of the disease when the compound is combined with another drug, compared to the effects obtained when the compound and the drug are used alone in single preparations.

First, the antidiabetic agent or antidiabetic complication agent that may be used in combination may, for example, include an insulin sensitivity enhancer, an α-glucosidase inhibitor, a biguanide compound, an insulin secretagogue, an insulin preparation, a glucagon receptor antagonist, an insulin receptor kinase agonist, a tripeptidyl peptidase II inhibitor, a dipeptidyl peptidase IV inhibitor, a protein tyrosine phosphatase 1B inhibitor, a glycogen phosphorylase inhibitor, a glucose-6-phosphatase inhibitor, a gluconeogenesis inhibitor, a fructose bisphosphatase inhibitor, a pyruvate dehydrogenase inhibitor, a glucokinase activator, D-chiro-inositol, a glycogen-like peptide-1 agonist, amyrin, an amyrin analog, an amyrin agonist, a glucocorticoid receptor antagonist, an 11α-hydroxysteroid dehydrogenase inhibitor, an aldose reductase inhibitor, a protein kinase C inhibitor, an α-aminobutyric acid receptor antagonist, a sodium channel antagonist, a transcription factor NF-αB inhibitor, an IKKα inhibitor, a lipid peroxidase inhibitor, an N-acetylated-alpha-linked acidic dipeptidase inhibitor, an insulin-like growth factor-I, a platelet-derived growth factor (PDGF), a platelet-derived growth factor (PDGF) analog, an endothelial growth factor (EGF), a nerve growth factor, a carnitine derivative, uridine, 5-hydroxy-1-methylhydantoin, EGB-761, bimoclomol, sulodexide, Y-128, TAR-428, etc.

More particularly, examples of the antidiabetic agent and the antidiabetic complication agent used herein may include the following drugs, but are not limited thereto.

The biguanide compound may include hydrochloric acid metformin, phenformin, etc.

Among insulin secretagogues, a sulfonylurea-based insulin secretagogue may, for example, include glyburide (glibenclamid), glipizide, gliclazide, chloropropamide, etc., and a non-sulfonylurea-based insulin secretagogue may include nateglinide, repaglinide, mitiglinide, etc.

The insulin preparation includes genetically recombinant human insulin, and animal-derived insulin. The insulin may be classified into three categories according to an action time, particularly classified into immediate-acting insulin (human insulin, human neutral insulin), intermediate-acting insulin (an insulin-human isophane insulin aqueous suspension, a human neutral insulin-human isophane insulin aqueous suspension, a human insulin zinc aqueous suspension, an insulin zinc aqueous suspension), and long-acting insulin (a human crystalline insulin zinc suspension).

The α-glucosidase inhibitor may include acarbose, voglibose, miglitol, etc.

The insulin sensitivity enhancer may include troglitazone, pioglitazone, rosiglitazone, MK-767 (KRP-297), tesaglitazar, LM4156, LY510929, TY-51501, GW-501516, etc.

The tripeptidyl peptidase II inhibitor may include UCL-139, etc.

The dipeptidyl peptidase IV inhibitor may include sitagliptin, vildagliptin, saxagliptin, linagliptin, anagliptin, alogliptin, gemigliptin, etc.

The aldose reductase inhibitor may include ascorbyl gamolenate, tolrestat, epalrestat, fidarestat, sorbinil, ponalrestrat, risarestat, zenarestat, etc.

The α-aminobutyric acid receptor antagonist may include topiramate, etc.

The sodium channel antagonist may include hydrochloric acid mexiletine, etc.

The transcription factor NF-αB inhibitor may include dexlipotam, etc.

The lipid peroxidase inhibitor may include tirilazad mesylate, etc.

The N-acetylated-alpha-linked acidic dipeptidase inhibitor may include GPI-5693, etc.

The carnitine derivative may include carnitine, levacecarnin hydrochloric acid, etc.

Next, the antihyperlipidemic agent and the antihypertensive agent that may be used in combination may, for example, include a hydroxymethylglutaryl coenzyme A reductase inhibitor, a fibrate-based compound, an α$_3$-adrenalin receptor agonist, an AMPK activator, an acyl coenzyme A:cholesterol acyltransferase inhibitor, probucol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor agonist, a nicotinic acid derivative, a bile acid sequestrant, a sodium-conjugated bile acid transporter inhibitor, a cholesterol ester transport protein inhibitor, an angiotensin converting enzyme inhibitor, an angiotensin II receptor antagonist, an endothelin converting enzyme inhibitor, an endothelin receptor antagonist, a diuretic agent, a calcium antagonist, a vasodilatory antihypertensive agent, a sympatholytic agent, a central antihypertensive agent, an α$_2$-adrenalin receptor agonist, an antiplatelet drug, a uric acid synthesis inhibitor, a uricosuric agent, a urine alkalizing agent, an anorexigenic agent, an ACE inhibitor, an adiponectin receptor agonist, a GPR40 agonist, a GPR40 antagonist, etc.

More particularly, examples of the antihyperlipidemic agent and the antihypertensive agent used herein may include the following drugs, but are not limited thereto.

The hydroxymethylglutaryl coenzyme A reductase inhibitor may include provastatin, lovastatin, pravastatin, cerivastatin, pitavastatin, etc.

The fibrate-based compound may include fenofibrate, bezafibrate, beclobrate, binifibrate, etc.

The squalene synthase inhibitor may include TAK-475, an α-phosphonosulfonate derivative (see U.S. Pat. No. 5,712, 396), etc.

The acyl coenzyme A:cholesterolacyltransferase inhibitor may include CI-1011, NTE-122, FCE-27677, RP-73163, MCC-147, DPU-129, etc.

The low-density lipoprotein receptor agonist may include MD-700, LY-295427, etc.

The microsomal triglyceride transfer protein inhibitor (MTP inhibitor) may include the compounds disclosed in U.S. Pat. Nos. 5,739,135, 5,712,279, and 5,760,246, etc.

The anorexigenic agent may include an adrenalin-noradrenalin agonist (mazindol, ephedrine, etc.), a serotonin agonist (a selective serotonin reuptake inhibitor, for example, fluvoxamine, etc.), an adrenalin-serotonin agonist (sibutramine, etc.), a melanocortin 4 receptor (MC4R) agonist, an α-melanocyte-stimulating hormone (α-MSH), leptin, a cocaine- and amphetamine-regulated transcript (CART), etc.

The thyroid hormone receptor agonist may include liothyronine sodium, levothyroxine sodium, etc.

The cholesterol absorption inhibitor may include ezetimibe, etc.

The lipase inhibitor may include orlistat, etc.

The carnitine palmitoyltransferase inhibitor may include etomoxir, etc.

The nicotinic acid derivative may include nicotinic acid, a nicotinic acid amide, nicomol, nicorandil, etc.

The angiotensin converting enzyme inhibitor may include captopril, enalapril maleate, alacepril, cilazapril, etc.

The angiotensin II receptor antagonist may include candesartan cilexetil, losartan potassium, eprosartan mesylate, etc.

The endothelin converting enzyme inhibitor may include CGS-31447, CGS-35066, etc.

For example, the compound according to one exemplary embodiment of the present invention is preferably used together with at least one drug selected from the group consisting of the insulin sensitivity enhancer, the α-glucosidase inhibitor, the biguanide compound, the insulin secretagogue, the insulin preparation, and the dipeptidyl peptidase IV inhibitor in order to treat diabetes, etc.

Also, the compound according to one exemplary embodiment of the present invention is preferably used together with at least one drug selected from the group consisting of the hydroxymethylglutaryl coenzyme A reductase inhibitor, the fibrate-based compound, the squalene synthase inhibitor, the acyl coenzyme A:cholesterol acyltransferase inhibitor, the low-density lipoprotein receptor agonist, the microsomal triglyceride transfer protein inhibitor, and the anorexigenic agent in order to treat hyperlipidemia, hypertension, etc.

The pharmaceutical composition according to one exemplary embodiment of the present invention includes the bicyclic derivative represented by Formula 1, or the pharmaceutically acceptable salt, isomer, hydrate or solvate thereof as an active ingredient. In this case, a typical pharmaceutically acceptable carrier, additive, or excipient may be added to the pharmaceutical composition, and the resulting mixture may then be formulated into a conventional preparation known in the art, for example, an oral or parenteral preparation such as a tablet, a capsule, a troche, a liquid, a suspension, etc.

A solid preparation for oral administration may be prepared by mixing at least one additive, for example, starch, calcium carbonate, sucrose, lactose, or gelatin, with one or more bicyclic derivatives according to one exemplary embodiment of the present invention. Also, a lubricating agent, such as magnesium stearate or talc, may be used in addition to these additives.

A suspension, a liquid for internal use, an emulsion, syrup, and the like may be used in a liquid preparation for oral administration. Also, various additives, for example, a wetting agent, a sweetening agent, a flavoring agent, a preservative, and the like may be used in addition to frequently used simple diluents such as water and liquid paraffin.

A sterile aqueous solution, a non-aqueous solvent, a suspending agent, an emulsion, a lyophilized preparation, a suppository, and the like are included in a preparation for parenteral administration.

A vegetable oil such as propylene glycol, polyethylene glycol, or olive oil; and an injectable ester such as ethyl oleate may be used as the non-aqueous solvent or the suspending agent, and Witepsol, Macrogol, Tween 61, cacao butter, laurin butter, glycerol, gelatin, and the like may be used as the suppository.

The dose of the pharmaceutical composition according to one exemplary embodiment of the present invention to be administered into the human body may vary depending on the age, body weight, and sex of a patient, the type of administration, the health condition, and the severity of a disease. The pharmaceutical composition may be generally administered to an adult patient weighing 70 kg at a dose of 0.1 mg/day to 400 mg/day, and more preferably, a dose of 1 mg/day to 100 mg/day, based on the weight of the active ingredient. In this case, the pharmaceutical composition may be administered once a day, or dividedly administered several times a day at constant time intervals.

Also, the present invention provides a use of the bicyclic derivative of Formula 1, or the pharmaceutically acceptable salt, isomer, hydrate or solvate thereof for the manufacture of a medicament for preventing or treating a disease or condition mediated by hyperglycemia.

Further, the present invention provides a method of preventing or treating a disease or condition mediated by hyperglycemia in a mammal, which includes administering the bicyclic derivative of Formula 1, or the pharmaceutically acceptable salt, isomer, hydrate or solvate thereof to the mammal.

Specific and preferred examples of the disease or condition mediated by hyperglycemia are the same as described above.

According to one exemplary method of preparing the compound of Formula 1 according to one exemplary embodiment of the present invention, a proper compound having a ring B defined above in Formula 1 is introduced into an intermediate, that is, a compound represented by Formula 3, to prepare a compound represented by Formula 2, and the compound of Formula 1 may be then prepared from the compound of Formula 2, as shown in the following Scheme 1.

[Scheme 1]

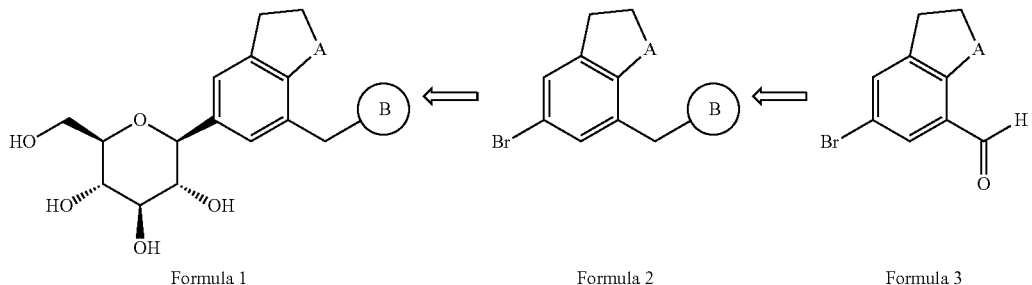

Formula 1      Formula 2      Formula 3

In Scheme 1, A and the ring B are the same as defined above in Formula 1.

The compound of Formula 3 in which A is —O—, i.e., 5-bromo-2,3-dihydrobenzofuran-7-carbaldehyde may be prepared in the synthetic pathway which is disclosed in WO 2006/082245 A1.

Further, the compound of Formula 3 in which A is —CH$_2$—, i.e., 5-bromo-2,3-dihydro-1H-indene-7-carbaldehyde may be prepared by subjecting 2,3-dihydro-1H-indene-5-amine used as a starting material to a four-step synthesis process, as shown in the following Scheme 2.

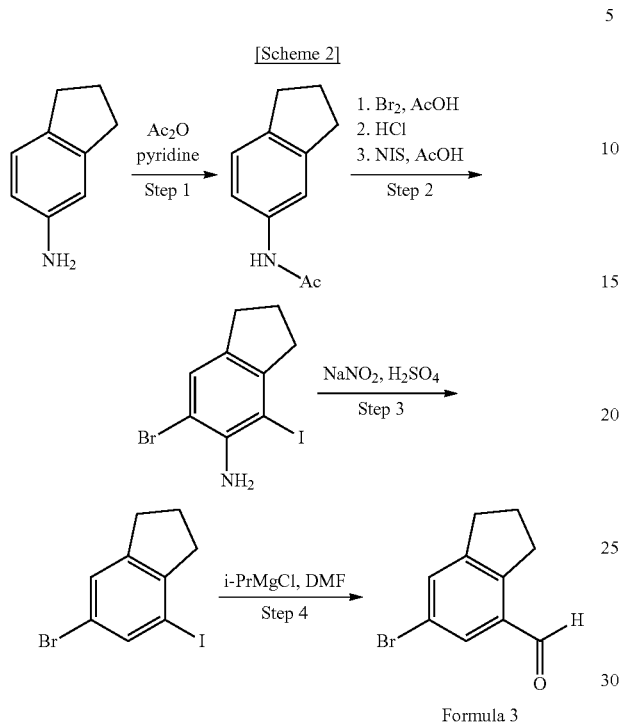

The compound of Formula 1 may be prepared from the compound of Formula 3, as shown in the following Scheme 3. In this case, the compound of Formula 1 may be deprotected in Step 5 using a method A or B selected according to the configuration of the ring B.

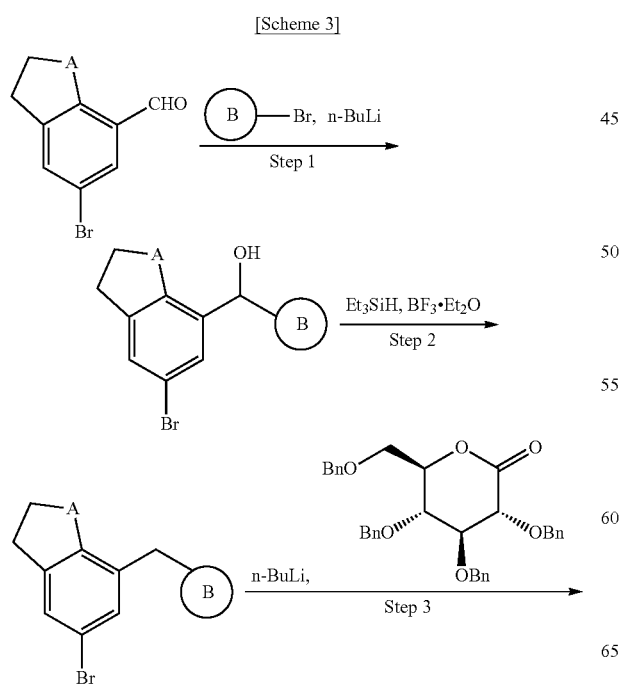

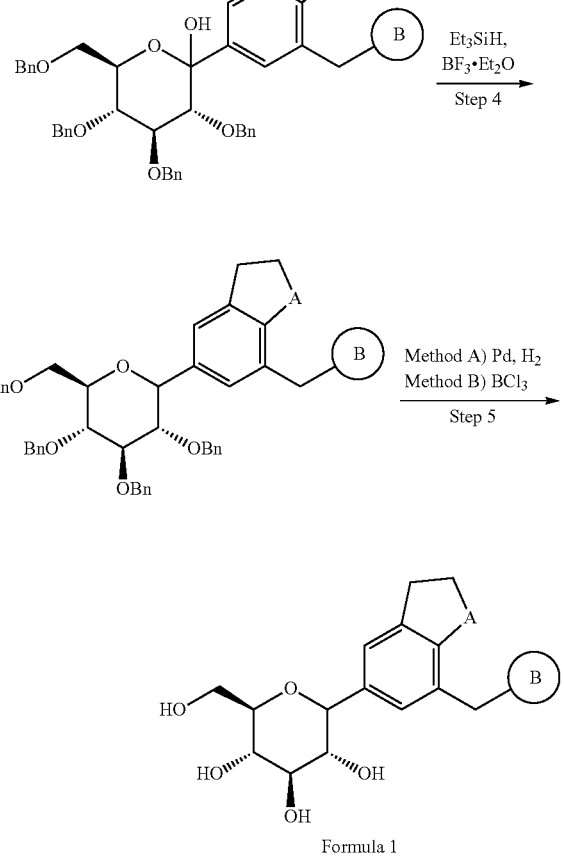

In Scheme 3, A and the ring B are the same as defined above in Formula 1.

According to one example of a specific method of preparing some of the compounds having a chemical structure of Formula 1, the compounds may be prepared as shown in the following Scheme 4 or 5.

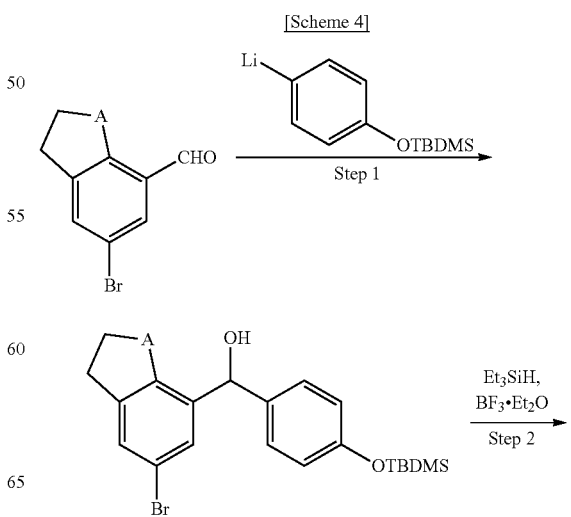

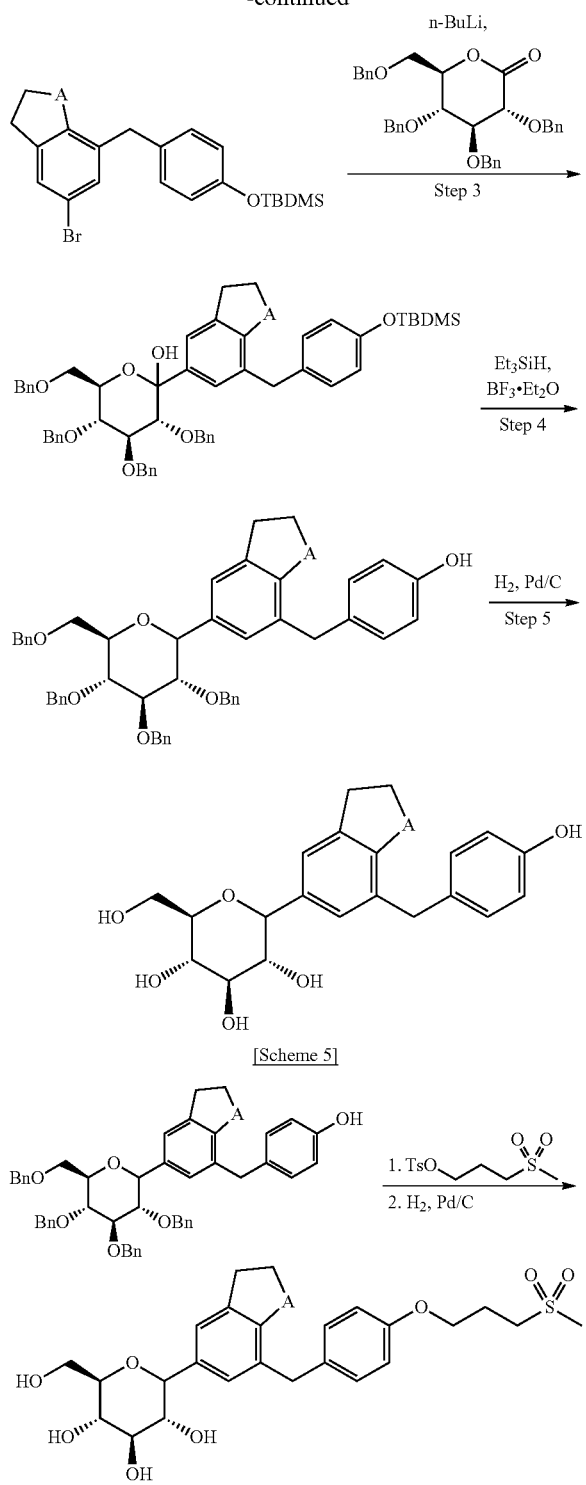

[Scheme 5]

In Schemes 4 and 5, A is the same as defined above in Formula 1.

Hereinafter, the present invention will be described in more detail with reference to the following examples. However, it should be understood that the detailed description herein is simply given by way of illustration of the present invention, and is not intended to limit the scope of the present invention.

PREPARATIVE EXAMPLE 1

Preparation of 6-bromo-2,3-dihydro-1H-indene-4-carbaldehyde

Step 1: N-(2,3-dihydro-1H-inden-5-yl)acetamide 5-aminoindan was dissolved in ethyl acetate (25 mL), and then cooled to 0° C. Ac$_2$O (4.2 g) and pyridine (3.25 g) were added dropwise thereto while stirring. The resulting mixture was stirred overnight at room temperature, and diethyl ether (40 mL) was added to the mixture, and stirred at 0° C. for an hour. The formed solid was filtered under reduced pressure to obtain a title compound (4.0 g).

$^1$H NMR spectra (300 MHz, CDCl$_3$): δ 7.43 (s, 1H), 7.26 (bs, 1H), 7.14 (s, 2H), 2.85 (m, 2H), 2.08 (s, 3H), 2.01 (m, 2H).

Step 2: 6-bromo-4-iodo-2,3-dihydro-1H-indene-5-amine

The compound N-(2,3-dihydro-1H-inden-5-yl)acetamide (4.0 g) synthesized in Step 1 was dissolved in acetic acid (60 mL), and then cooled until the inner temperature reached 4° C. Bromine (1.4 mL) was slowly added dropwise while maintaining the inner temperature in a range of 4 to 5° C. The resulting solution was stirred in a range of 4 to 5° C. for an hour, and it was checked as to whether the reaction was completed. Thereafter, a saturated ammonium chloride solution was added to the reaction solution, and the reaction solution was warmed to room temperature, and extracted with ethyl acetate. An organic layer was washed with water and brine, dried using anhydrous magnesium sulfate, and then filtered. An organic solvent was removed under reduced pressure, and 50 mL of ethanol and 12N hydrochloric acid (50 mL) were added dropwise. The resulting mixture was stirred under reflux for 3 hours, and it was checked as to whether the reaction was completed. Then, the mixture was cooled to room temperature. A 10% potassium hydroxide solution was added to the reaction solution, and extracted with dichloromethane. An organic layer was washed with brine, dried using anhydrous magnesium sulfate, and then filtered. The organic solvent was removed under reduced pressure, and acetic acid (40 mL) was added to dissolve a residue. Subsequently, N-iodosuccinimide (5.8 g) was subdivided and added dropwise to the reaction solution. The reaction solution was stirred overnight at room temperature. After it was confirmed that the reaction was completed, water was added to the reaction solution, and the reaction solution was extracted with dichloromethane. The extract was dried with anhydrous magnesium sulfate, filtered to remove the organic solvent under reduced pressure, and purified by column chromatography to obtain a title compound (3.5 g).

$^1$H NMR spectra (300 MHz, CDCl$_3$): δ 7.23 (s, 1H), 2.99 (t, 2H), 2.83 (t, 2H), 2.08 (m, 2H).

Step 3: 6-bromo-4-iodo-2,3-dihydro-1H-indene

The compound 6-bromo-4-iodo-2,3-dihydro-1H-indene-5-amine (3.5 g) synthesized in Step 2 and NaNO$_2$ (1.07 g) were dissolved in ethanol (100 mL), and then cooled to 0° C. Sulfuric acid (52 mL) was slowly added dropwise to the reaction solution, and the reaction solution was stirred for 3 hours under reflux conditions. It was confirmed that the reaction was completed, and then the resulting reaction solution was cooled at room temperature. Water was added to the reaction solution, and the reaction solution was extracted with dichloromethane. The extract was dried using anhydrous magnesium sulfate, filtered to remove the organic solvent under reduced pressure, and then purified by column chromatography to obtain a title compound (2.3 g).

$^1$H NMR spectra (300 MHz, CDCl$_3$): δ 7.65 (s, 1H), 7.29 (s, 1H), 3.04 (t, 2H), 2.80 (t, 2H), 2.07 (m, 2H).

Step 4:
6-bromo-2,3-dihydro-1H-indene-4-carbaldehyde 6-bromo-4-iodo-2,3-dihydro-1H-indene (2.3 g) was dissolved in tetrahydrofuran (10 mL), and then cooled to a temperature of −20° C. A 2.0 M isopropylmagnesium chloride solution (3.9 mL) was slowly added to the reaction solution, and the reaction solution was stirred at −20° C. for 3 hours. Dimethylformamide (0.78 g) was slowly added thereto. The resulting mixture was warmed to room temperature, and then stirred overnight. After it was confirmed that the reaction was completed, a saturated ammonium chloride solution was added to the reaction solution, and the reaction solution was warmed to room temperature, and then extracted with ethyl acetate. An organic layer was washed with water and brine, dried using anhydrous magnesium sulfate, and then filtered. The organic solvent was removed under reduced pressure, and the filtrate was purified by column chromatography to obtain a title compound (1.2 g).

$^1$H NMR spectra (300 MHz, CDCl$_3$): δ 10.9 (s, 1H), 7.75 (s, 1H), 7.59 (s, 1H), 3.22 (t, 2H), 2.93 (t, 2H), 2.16 (m, 2H).

EXAMPLE 1

Preparation of (2S,3R,4R,5S,6R)-2-(7-(4-ethoxybenzyl)-2,3-dihydrobenzofuran-5-yl)-6-hydroxymethyl-tetrahydro-2H-pyran-3,4,5-triol

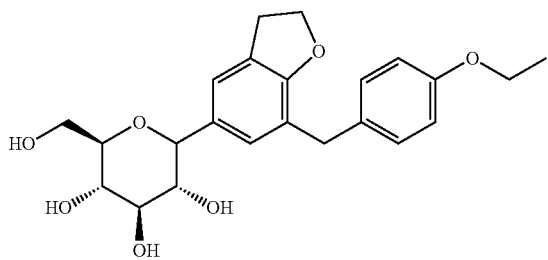 [SMILES: CCOc1ccc(Cc2cc(C3O[C@H](CO)[C@@H](O)[C@H](O)[C@H]3O)cc3c2OCC3)cc1]

Step 1: Preparation of (5-bromo-2,3-dihydrobenzofuran-7-yl)(4-ethoxyphenyl)methanol 1-bromo-4-ethoxy benzene (743 mg) was dissolved in 20 ml of tetrahydrofuran (THF), and cooled to a temperature of −78° C. An n-butyllithium (n-BuLi) solution (2.32 ml) was slowly added while stirring, and the reaction solution was stirred at −78° C. for 30 minutes. 5-bromo-2,3-dihydrobenzofuran-7-carbaldehyde (400 mg) (the synthetic pathway is disclosed in WO 2006/082245 A1) dissolved in 5 ml of THF was slowly added to the reaction solution, and the reaction solution was stirred at −78° C. for 2 hours. A saturated NH$_4$Cl solution was added to the reaction solution, and the reaction solution was warmed to room temperature, and then extracted with ethyl acetate. An organic layer was washed with water and brine, dried using MgSO$_4$, and then filtered. The organic solvent was removed under reduced pressure, and the filtrate was then purified by column chromatography to obtain a title compound (400 mg).

$^1$H NMR spectra (300 MHz, CDCl$_3$): δ 7.33 (s, 1H), 7.29 (d, 2H), 7.23 (s, 1H), 6.87 (d, 2H), 5.86 (d, 1H), 4.60 (t, 2H), 4.05 (q, 2H), 3.20 (t, 2H), 2.69 (d, 1H), 1.42 (t, 3H).

Step 2: Preparation of 5-bromo-7-(4-ethoxybenzyl)-2,3-dihydrobenzofuran

The compound (400 mg) obtained in Step 1 was dissolved in CH$_2$Cl$_2$ (10 ml), and then was cooled under an argon atmosphere until the inner temperature reached −50° C. Et$_3$SiH (0.55 ml) and BF$_3$.Et$_2$O (0.22 ml) were sequentially added to the reaction solution, and the reaction solution was stirred at the same temperature for 10 minutes. After the reaction temperature increased to 0° C., the reaction solution was stirred for an hour. Sodium bicarbonate was added to the reactant, and an organic layer was then extracted. The organic layer was washed with water and brine, dried using anhydrous magnesium sulfate, and then filtered. The organic solvent was removed under reduced pressure, and the filtrate was then purified by column chromatography to obtain a title compound (290 mg).

$^1$H NMR spectra (300 MHz, CDCl$_3$): δ 7.10 (t, 3H), 6.96 (s, 1H), 6.82 (d, 2H), 4.57 (t, 2H), 4.02 (q, 2H), 3.79 (s, 2H), 3.20 (t, 2H), 1.40 (t, 3H).

Step 3: Preparation of (3R,4S,5R,6R)-3,4,5-tris (benzyloxy)-6-(benzyloxymethyl)-2-(7-(4-ethoxybenzyl)-2,3-dihydrobenzofuran-5-yl)-tetrahydro-2H-pyran-2-ol The compound (290 mg) obtained in Step 2 was dissolved in 10 ml of anhydrous tetrahydrofuran, and then cooled until the inner temperature reached −78° C. An n-BuLi solution (0.54 ml) was slowly added while stirring, and the reaction solution was stirred at −78° C. for 30 minutes. (3R,4S,5R,6R)-3,4,5-tris(benzyloxy)-6-((benzyloxy)methyl)tetrahydro-2H-pyran-2-one (468 mg) dissolved in 5 ml of THF was slowly added to the reaction solution, and then the reaction solution was stirred at −78° C. for 2 hours. A saturated NH$_4$Cl solution was added to the reaction solution, warmed to room temperature, and then extracted with ethyl acetate. An organic layer was washed with water and brine, dried using MgSO$_4$, and then filtered. The organic solvent was removed under reduced pressure, and the filtrate was then purified by column chromatography to obtain a title compound (462 mg).

$^1$H NMR spectra (300 MHz, CDCl$_3$): δ 7.33-7.10 (m, 20H), 7.10 (d, 2H), 6.96 (d, 2H), 6.73 (d, 2H), 4.88 (s, 2H), 4.67-4.55 (m, 5H), 4.39 (d, 1H), 4.11 (m, 1H), 4.04 (t, 1H), 3.93-3.82 (m, 4H), 3.69 (m, 3H), 3.20 (t, 3H), 1.40 (t, 3H).

Step 4: Preparation of 7-(4-ethoxybenzyl)-5-((2S,3S,4R,5R,6R)-3,4,5-tris(benzyloxy)-6-(benzyloxymethyl)-tetrahydro-2H-pyran-2-yl)-2,3-dihydrobenzofuran The compound (462 mg) obtained in Step 3 was dissolved in CH$_2$Cl$_2$ (20 ml), and then cooled under an argon atmosphere until the inner temperature reached −50° C. Et$_3$SiH (0.28 ml) and BF$_3$.Et$_2$O (0.11 ml) were added while stirring, and then the reaction solution was stirred at the same temperature for 10 minutes. The reaction solution was stirred at 0° C. for an hour, and extracted while adding sodium bicarbonate. An organic layer was washed with water and brine, dried using MgSO$_4$, and then filtered. The filtrate was purified by column chromatography to obtain a title compound (320 mg).

$^1$H NMR spectra (300 MHz, CDCl$_3$): δ 7.32-7.07 (m, 21H), 6.95 (s, 1H), 6.89 (d, 2H), 6.74 (d, 2H), 4.87 (t, 3H), 4.59 (m 5H), 4.31 (d, 2H), 4.11 (d, 2H), 3.85-3.70 (m, 9H), 3.55 (m, 2H), 3.19 (m, 2H), 1.36 (t, 3H).

Step 5: Preparation of (2S,3R,4R,5S,6R)-2-(7-(4-ethoxybenzyl)-2,3-dihydrobenzofuran-5-yl)-6-hydroxymethyl-tetrahydro-2H-pyran-3,4,5-triol The compound (320 mg) obtained in Step 4 was dissolved in 30 ml of EA/MeOH (=2/3) and 10% Pd/C (32 mg) was then added to the reaction solution. The reaction solution was stirred for 12 hours under a hydrogen atmosphere. The reaction solution was dried and filtered. The filtrate was purified by column chromatography to obtain a title compound (100 mg).

$^1$H NMR spectra (300 MHz, MeOD): δ 7.10 (d, 2H), 7.06 (s, 1H), 6.86 (s, 1H), 6.77 (d, 2H), 4.54 (t, 2H), 4.04-3.92 (m, 3H), 3.87-3.75 (m, 4H), 3.63 (t, 2H), 3.47 (m, 2H), 3.16 (t, 2H), 1.36 (t, 3H).

MS (ESI$^+$, m/z): [M+NH$_4$]$^+$ m/z 434.2171, [M+K]$^+$ m/z 455.1467

The following compounds of Examples 2 to 11 were synthesized in the same synthetic pathway as in Example 1.

TABLE 1

| Example | Compound name/Structural formula/Analysis data |
|---|---|
| 2 | (2S,3R,4R,5S,6R)-2-(7-(4-ethylbenzyl)-2,3-dihydrobenzofuran-5-yl)-6-hydroxymethyl-tetrahydro-2H-pyran-3,4,5-triol 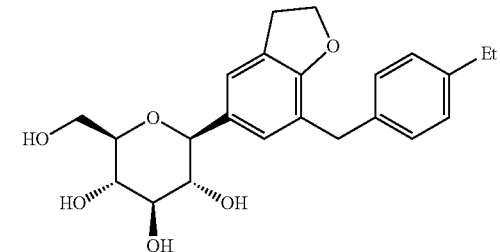 [SMILES: CCc1ccc(Cc2cc([C@@H]3O[C@H](CO)[C@@H](O)[C@H](O)[C@H]3O)cc3c2OCC3)cc1] $^1$H NMR spectra (300 MHz, CDCl$_3$): δ 7.21 (dd, 1H), 7.09 (d, 2H), 7.06 (s, 1H), 6.92 (s, 1H), 6.88 (d, 2H), 4.52 (t, 2H), 4.01 (d, 1H), 3.86-3.70 (m, 6H), 3.61 (m, 2H), 3.46 (m, 2H), 3.14 (t, 2H), 2.54 (q, 2H), 1.15 (t, 3H) MS (ESI$^+$, m/z): [M + NH$_4$]$^+$ m/z 418.2131, [M + K]$^+$ m/z 439.1418 |
| 3 | (2R,3S,4R,5R,6S)-2-hydroxymethyl-6-(7-(4-n-propylbenzyl)-2,3-dihydrobenzofuran-5-yl)-tetrahydro-2H-pyran-3,4,5-triol 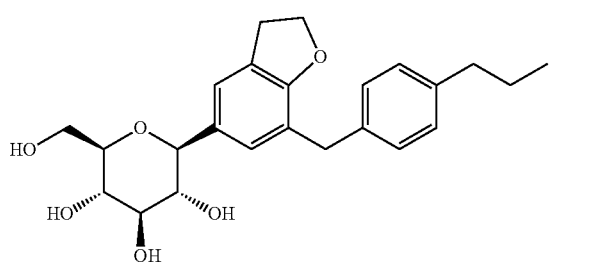 [SMILES: CCCc1ccc(Cc2cc([C@@H]3O[C@H](CO)[C@@H](O)[C@H](O)[C@H]3O)cc3c2OCC3)cc1] $^1$H NMR spectra (300 MHz, MeOD) δ 7.14-7.12 (m, 3H), 7.07-7.02 (m, 2H), 6.98 (s, 1H), 4.54 (t, 2H), 4.00 (d, 1H), 3.83 (m, 2H), 3.64 (m, 1H), 3.46-3.19 (m, 5H), 3.16 (t, 2H), 2.51 (t, 2H), 1.59-1.61 (m, 2H), 0.92 (t, 3H). MS (ESI$^+$, m/z): [M + NH$_4$]$^+$ m/z 432.2383, [M + K]$^+$ m/z 453.1681 |

TABLE 1-continued

| Example | Compound name/Structural formula/Analysis data |
|---|---|
| 4 | (2R,3S,4R,5R,6S)-2-hydroxymethyl-6-(7-(4-trifluoromethylbenzyl)-2,3-dihydrobenzofuran-5-yl)tetrahydro-2H-pyran-3,4,5-triol |

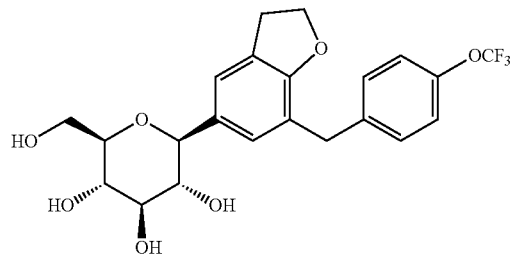 [SMILES: OC[C@H]1O[C@@H](c2cc3c(c(Cc4ccc(OC(F)(F)F)cc4)c2)OCC3)[C@H](O)[C@@H](O)[C@@H]1O]

$^1$H NMR spectra (300 MHz, MeOD) δ 7.39 (d, 2H), 7.25 (d, 2H), 7.07 (s, 1H), 6.89 (s, 1H), 4.42 (t, 2H), 3.97 (d, 1H), 3.84 (d, 2H) 3.70 (s, 2H), 3.55 (m, 3H), 3.23 (d, 1H), 3.02 (t, 2H).
MS (ESI$^+$, m/z): [M + NH$_4$]$^+$ m/z 458.1786, [M + K]$^+$ m/z 479.1079

| 5 | (2R,3S,4R,5R,6S)-2-hydroxymethyl-6-(7-(4-trifluoromethoxybenzyl)-2,3-dihydrobenzofuran-5-yl)tetrahydro-2H-pyran-3,4,5-triol |

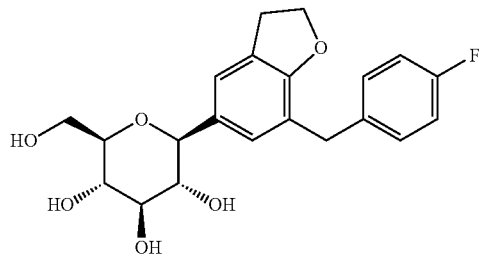 [SMILES: OC[C@H]1O[C@@H](c2cc3c(c(Cc4ccc(F)cc4)c2)OCC3)[C@H](O)[C@@H](O)[C@@H]1O]

$^1$H NMR spectra (300 MHz, MeOD) δ 7.32 (d, 2H), 7.17-7.11 (m, 3H), 7.02 (s, 1H), 4.54 (t, 2H), 4.02 (d, 1H), 3.91-3.85 (m, 3H), 3.47 (m, 1H), 3.38-3.20 (m, 4H), 3.17 (t, 2H).
MS (ESI$^+$, m/z): [M + NH$_4$]$^+$ m/z 474.1740, [M + K]$^+$ m/z 495.1034

| 6 | (2S,3R,4R,5S,6R)-2-(7-(4-fluorobenzyl)-2,3-dihydrobenzofuran-5-yl)-6-(hydroxymethyl)tetrahydro-2H-pyran-3,4,5-triol |

$^1$H NMR spectra (300 MHz, CDCl$_3$) δ 7.19-7.10 (m, 3H), 6.96-6.88 (m, 3H), 4.56 (t, 2H), 4.06 (d, 1H), 3.92-3.43 (m, 8H), 3.19 (t, 3H).
MS (ESI$^+$, m/z): [M + NH$_4$]$^+$ m/z 408.1827, [M + K]$^+$ m/z 429.1119

| Example | Compound name/Structural formula/Analysis data |
|---|---|
| 7 | (2S,3R,4R,5S,6R)-2-(7-((2,3-dihydrobenzo[b][1,4]dioxin-6-yl)methyl)-2,3-dihydrobenzofuran-5-yl)-6-(hydroxymethyl)tetrahydro-2H-pyran-3,4,5-triol<br>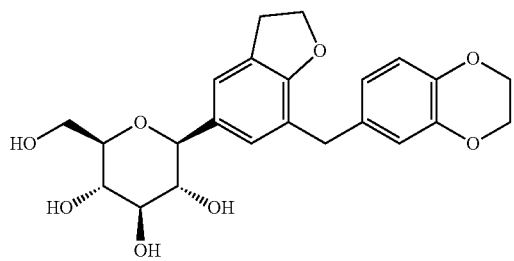<br>$^1$H NMR spectra (300 MHz, MeOD) δ 7.01 (s, 1H), 6.84 (s, 1H), 6.56 (s, 3H), 4.38 (t, 2H), 4.04 (s, 4H), 3.89 (d, 1H), 3.64-3.57 (m, 4H), 3.31-3.19 (m, 3H), 3.04 (t, 3H).<br>MS (ESI$^+$, m/z): [M + NH$_4$]$^+$ m/z 448.1967, [M + K]$^+$ m/z 469.1259 |
| 8 | (2S,3R,4R,5S,6R)-2-(7-(4-(cyclopropylmethoxy)benzyl)-2,3-dihydrobenzofuran-5-yl)-6-(hydroxymethyl)tetrahydro-2H-pyran-3,4,5-triol<br>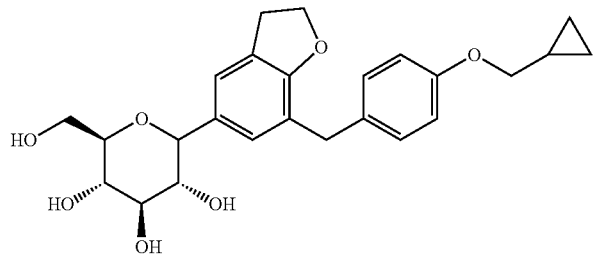 [SMILES: OC[C@H]1OC(c2cc3c(c(Cc4ccc(OCC5CC5)cc4)c2)OCC3)[C@H](O)[C@@H](O)[C@@H]1O]<br>$^1$H NMR spectra (300 MHz, MeOD) δ 7.21 (dd, 1H), 7.09 (d, 2H), 7.06 (s, 1H), 6.92 (s, 1H), 6.88 (d, 2H), 4.52 (t, 2H), 4.01 (d, 1H), 3.86-3.70 (m, 6H), 3.61 (m, 2H), 3.46 (m, 2H), 3.14 (t, 2H) 1.23 (m, 1H), 0.59 (m, 2H), 0.31 (m, 2H).<br>MS (ESI$^+$, m/z): [M + NH$_4$]$^+$ m/z 460.2334, [M + K]$^+$ m/z 481.1623 |
| 9 | (2S,3R,4R,5S,6R)-2-(7-(4-ethoxy-3-fluorobenzyl)-2,3-dihydrobenzofuran-5-yl)-6-(hydroxymethyl)tetrahydro-2H-pyran-3,4,5-triol<br>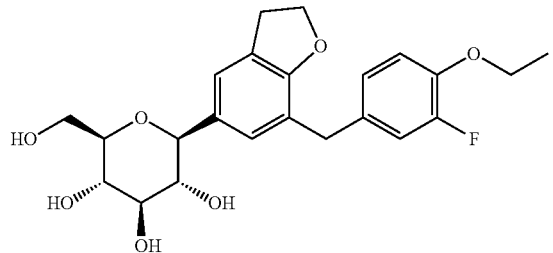 [SMILES: CCOc1ccc(Cc2cc([C@@H]3O[C@H](CO)[C@@H](O)[C@H](O)[C@H]3O)cc3c2OCC3)cc1F]<br>$^1$H NMR spectra (300 MHz, CDCl$_3$) δ 7.08 (s, 1H), 6.95-6.86 (m, 3H), 6.80 (t, 1H), 4.52 (t, 2H), 4.14 (br, 1H), 4.05-3.98 (m, 3H), 3.94 (br, 1H), 3.84-3.58 (m, 6H), 3.51-3.48 (m, 1H), 3.38-3.35 (m, 1H), 2.85 (br, 1H), 2.57 (br, 1H), 1.39 (t, 3H).<br>MS (ESI$^+$, m/z): [M + NH$_4$]$^+$ 452.2075, [M + K]$^+$ m/z 473.1371 |

TABLE 1-continued

| Example | Compound name/Structural formula/Analysis data |
|---|---|
| 10 | (2S,3R,4R,5S,6R)-2-(7-(4-ethoxy-2-fluorobenzyl)-2,3-dihydrobenzofuran-5-yl)-6-(hydroxymethyl)tetrahydro-2H-pyran-3,4,5-triol 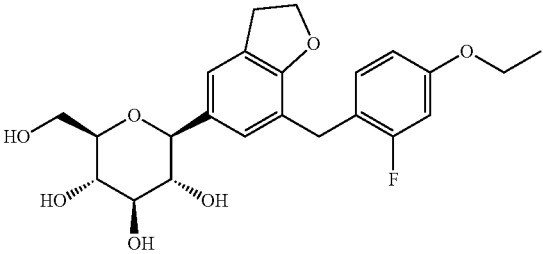 [SMILES: CCOc1ccc(Cc2cc([C@@H]3O[C@H](CO)[C@@H](O)[C@H](O)[C@H]3O)cc3c2OCC3)c(F)c1] $^1$H NMR spectra (300 MHz, CDCl$_3$) δ 7.08-7.02 (m, 2H), 6.89 (s, 1H), 6.58-6.53 (m, 2H), 4.53 (t, 2H), 4.03 (d, 1H), 3.97-3.90 (m, 3H), 3.82-3.59 (m, 7H), 3.47 (t, 1H), 3.39-3.36 (m, 1H), 3.14 (t, 1H), 2.64 (br, 1H), 2.42 (br, 1H), 1.36 (t, 3H). MS (ESI$^+$, m/z): [M + NH$_4$]$^+$ m/z 452.2075, [M + K]$^+$ m/z 473.1371 |
| 11 | (2S,3R,4R,5S,6R)-2-(7-(4-hydroxybenzyl)-2,3-dihydrobenzofuran-5-yl)-6-(hydroxymethyl)tetrahydro-2H-pyran-3,4,5-triol 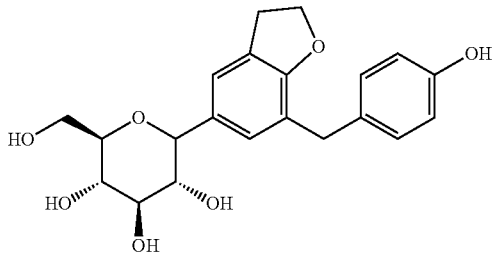 [SMILES: OC[C@H]1OC(c2cc3c(c(Cc4ccc(O)cc4)c2)OCC3)[C@H](O)[C@@H](O)[C@@H]1O] $^1$H NMR spectra (300 MHz, MeOD) δ 7.01 (s, 1H), 6.94 (d, 2H), 6.84 (s, 1H), 6.55 (d, 2H), 4.40 (t, 2H), 3.67 (d, 2H), 3.48-3.20 (m, 7H), 3.01 (t, 2H). MS (ESI$^+$, m/z): [M + NH$_4$]$^+$ m/z 406.1858, [M + K]$^+$ m/z 427.1156 |

EXAMPLE 12

Preparation of (2S,3S,4R,5R,6S)-2-(hydroxymethyl)-6-(7-(4-(3-(methylsulfonyl)propoxy)benzyl)-2,3-dihydrofuran-5-yl)tetrahydro-2H-pyran-3,4,5-triol

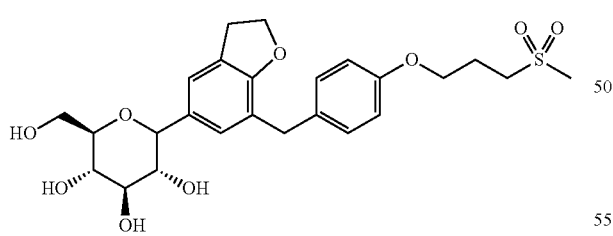

The compound (70 mg, 0.09 mmol) obtained in Step 4 of Example 11 was dissolved in 2 mL of dimethylformamide, and 1-bromo-3-(methylsulfonyl)propane (35.5 mg, 0.12 mmol) and potassium carbonate (17.4 mg, 0.13 mmol) were added thereto. The reaction solution was then stirred at 100° C. for 48 hours. Water was added to the reaction solution, and the reaction solution was extracted with ethyl acetate. An organic layer was dried using anhydrous magnesium sulfate, and the solvent was concentrated to obtain 7-(4-(3-(methylsulfonyl)propoxy)benzyl)-5-((2S,3S,4R,5R,6R)-3,4,5-tris(benzyloxy)-6-((benzyloxy)methyl)tetrahydro-2H-pyran-2-yl)-2,3-dihydrobenzofuran. The compound was subjected to the same procedure as in Step 5 of Example 1, without performing further purification process, to obtain a title compound (7 mg).

$^1$H NMR spectra (300 MHz, MeOD): δ 7.04-7.01 (m, 3H), 6.84 (s, 1H), 6.69 (d, 2H), 4.43 (t, 2H), 3.98-3.89 (m, 3H), 3.73-3.69 (m, 4H), 3.30-3.16 (m, 6H), 3.05 (t, 2H), 2.89 (s, 3H), 2.13 (m, 2H).

MS (ESI$^+$, m/z): [M+NH$_4$]$^+$ m/z 526.2118

EXAMPLE 13

Preparation of (2S,3R,4R,5S,6R)-2-(7-(4-ethoxybenzyl)-2,3-dihydro-1H-inden-5-yl)-6-(hydroxymethyl)tetrahydro-2H-pyran-3,4,5-triol

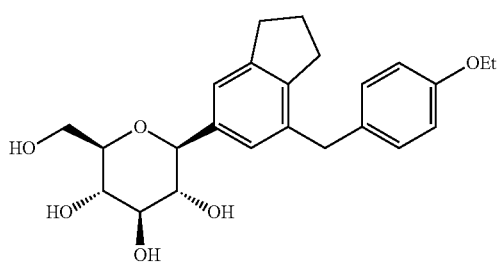 [SMILES: CCOc1ccc(Cc2cc([C@@H]3O[C@H](CO)[C@@H](O)[C@H](O)[C@H]3O)cc3c2CCC3)cc1]

Step 1: 6-bromo-4-(4-ethoxybenzyl)-2,3-dihydro-1H-indene 1-bromo-4-ethoxybenzene (910 mg) was dissolved in tetrahydrofuran (20 mL), and then cooled to a temperature of −78° C. An n-BuLi solution (3.1 mL) was slowly added while stirring, and the reaction solution was stirred at −78° C. for 30 minutes. The 6-bromo-2,3-dihydro-1H-indene-4-carbaldehyde (510 mg) prepared in Preparative Example 1 was dissolved in tetrahydrofuran (5 mL), which was then slowly added to the reaction solution. The reaction solution was stirred at −78° C. for 2 hours. A saturated ammonium chloride solution was added to the reaction solution, warmed to room temperature, and then extracted with ethyl acetate. An organic layer was washed with water and brine, dried using anhydrous magnesium sulfate, and then filtered. The organic solvent was removed under reduced pressure, and the filtrate was dried under reduced pressure. Dichloromethane (10 mL) was added under an argon atmosphere to dissolve the residue, and then cooled under the argon atmosphere until the inner temperature reached −50° C. Triethylsilane (1.63 mL) and boron trifluoride diethyl etherate (0.43 mL) were sequentially added to the reactant, and then the reactant was stirred at the same temperature for 10 minutes. After the reaction temperature increased to 0° C., the reactant was stirred for an hour. Sodium bicarbonate was added to the reactant, and an organic layer was then extracted. The organic layer was washed with water and brine, dried using anhydrous magnesium sulfate, and then filtered. The organic solvent was removed under reduced pressure, and the filtrate was purified by column chromatography to obtain a title compound (530 mg).

$^1$H NMR spectra (300 MHz, CDCl$_3$): δ 7.22 (s, 1H), 7.08-7.02 (m, 2H), 6.95-6.90 (m, 1H), 6.80-6.78 (m, 2H), 4.07-3.99 (m, 2H), 3.82 (s, 2H), 2.88 (t, 2H), 2.69 (t, 2H), 2.01 (q, 2H), 1.30 (t, 2H).

Step 2: (2R,3R,4R,5S,6S)-3,4,5-tris(benzyloxy)-2-((benzyloxy)methyl)-6-(7-(4-ethoxymethylbenzyl)-2,3-dihydro-1H-inden-5-yl)tetrahydro-2H-pyran The compound 6-bromo-4-(4-ethoxybenzyl)-2,3-dihydro-1H-indene (530 mg) obtained in Step 1 was dissolved in 10 mL of anhydrous tetrahydrofuran, and then cooled until the inner temperature reached −78° C. An n-butyllithium solution (1.22 mL) was slowly added to the reaction solution, and then the reaction solution was stirred at −78° C. for an hour. (3R,4S,5R,6R)-3,4,5-tris(benzyloxy)-6-((benzyloxy)methyl)tetrahydro-2H-pyran-2-one (720 mg) dissolved in tetrahydrofuran (5 mL) was slowly added to the reaction solution, and then the reaction solution was stirred at −78° C. for 2 hours. A saturated ammonium chloride solution was added to the reaction solution, warmed to room temperature, and then extracted with ethyl acetate. An organic layer was washed with water and brine, dried using anhydrous magnesium sulfate, and then filtered. The organic solvent was removed under reduced pressure, and the filtrate was dried under reduced pressure. Dichloromethane (20 mL) was added under an argon atmosphere to dissolve the residue, and then cooled until the inner temperature reached −50° C. Triethylsilane (0.62 mL) and boron trifluoride diethyl etherate (0.24 mL) were added to the reaction solution, and then the reaction solution was stirred at the same temperature for 10 minutes. After the reaction temperature increased to 0° C., the reactant was stirred for an hour. Sodium bicarbonate was added to the reactant, and an organic layer was then extracted. The organic layer was washed with water and brine, dried using anhydrous magnesium sulfate, and then filtered. The organic solvent was removed under reduced pressure, and the filtrate was then purified by column chromatography to obtain a title compound (510 mg).

$^1$H NMR spectra (300 MHz, CDCl$_3$): δ 7.34-6.99 (m, 22H), 6.99-6.89 (m, 2H), 6.70 (d, 2H), 4.92-4.86 (m, 3H), 4.66-4.64 (m, 3H), 4.34 (d, 1H), 3.96-3.77 (m, 8H), 3.58 (m, 2H), 2.88 (m, 2H), 2.76 (m, 2H), 2.02 (m, 2H), 1.36 (t, 3H).

Step 3: (2S,3R,4R,5S,6R)-2-(7-(4-ethoxybenzyl)-2,3-dihydro-1H-inden-5-yl)-6-(hydroxymethyl)tetrahydro-2H-pyran-3,4,5-triol The compound (2R,3R,4R,5S,6S)-3,4,5-tris(benzyloxy)-2-((benzyloxy)methyl)-6-(7-(4-ethoxymethylbenzyl)-2,3-dihydro-1H-inden-5-yl)tetrahydro-2H-pyran (510 mg) obtained in Step 2 was dissolved in ethyl acetate/methanol (2:3, 30 mL), and 10% palladium (150 mg) was then added to the reaction solution. The reaction solution was stirred for 12 hours under a hydrogen atmosphere. The reaction solution was filtered under reduced pressure, and then purified by column chromatography to obtain a title compound (175 mg).

$^1$H NMR spectra (300 MHz, MeOD): δ 7.07 (s, 1H), 7.04-7.03 (m, 3H), 6.80-6.77 (d, 2H), 4.12 (d, 1H), 3.97 (q, 2H), 3.87-3.86 (m, 2H), 3.68-3.65 (m, 1H), 3.45-3.32 (m, 5H), 2.89 (t, 2H), 2.75 (t, 2H), 2.09 (t, 2H), 1.36 (t, 3H).

MS (ESI$^+$, m/z): [M+NH$_4$]$^+$ m/z 432.2390

The following compounds of Examples 14 to 35 were synthesized in the same synthetic pathway as in Example 13.

TABLE 2

| Example | Compound name/Structural formula/Analysis data |
| --- | --- |
| 14 | (2R,3S,4R,5R,6S)-2-(hydroxymethyl)-6-(7-(4-methoxybenzyl)-2,3-dihydro-1H-inden-5-yl)tetrahydro-2H-pyran-3,4,5-triol |

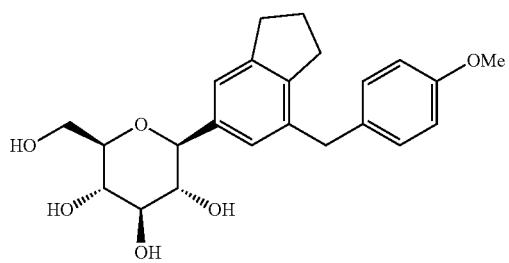 [SMILES: COc1ccc(Cc2cc([C@@H]3O[C@H](CO)[C@@H](O)[C@H](O)[C@H]3O)cc3c2CCC3)cc1]

$^1$H NMR spectra (300 MHz, CDCl$_3$): δ 7.13 (s, 1H), 7.05 (d, 2H), 6.93 (s, 1H), 6.80 (d, 2H), 4.13 (d, 1H), 3.91-3.87 (m, 5H), 3.76 (s, 3H), 3.73-3.53 (m, 3H), 3.56-3.48 (m, 2H), 2.90 (t, 2H), 2.76 (t, 2H), 2.08-2.00 (m, 2H)

MS (ESI$^+$, m/z): [M + NH$_4$]$^+$ m/z 418.2225

TABLE 2-continued

| Example | Compound name/Structural formula/Analysis data |
|---|---|
| 15 | (2R,3S,4R,5R,6S)-2-(hydroxymethyl)-6-(7-(4-methylbenzyl)-2,3-dihydro-1H-inden-5-yl)tetrahydro-2H-pyran-3,4,5-triol |

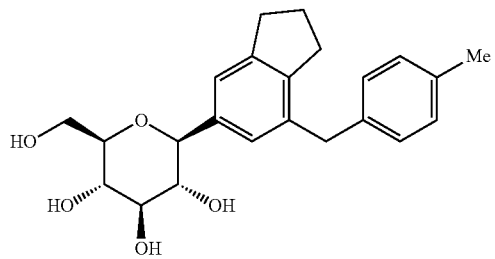 [SMILES: Cc1ccc(Cc2cc([C@@H]3O[C@H](CO)[C@@H](O)[C@H](O)[C@H]3O)cc3c2CCC3)cc1]

$^1$H NMR spectra (300 MHz, MeOD) δ 7.17 (s, 1H), 7.04 (m, 5H), 4.10 (d, 1H), 3.89-3.87 (m, 3H), 3.73-3.69 (m, 1H), 3.49-3.32 (m, 4H), 2.88 (t, 2H), 2.71 (t, 2H), 2.28 (s, 3H), 1.97 (t, 2H)
MS (ESI$^+$, m/z): [M + NH$_4$]$^+$ m/z 402.2285

| | |
|---|---|
| 16 | (2S,3R,4R,5S,6R)-2-(7-(4-ethylbenzyl)-2,3-dihydro-1H-inden-5-yl)-6-(hydroxymethyl)tetrahydro-2H-pyran-3,4,5-triol |

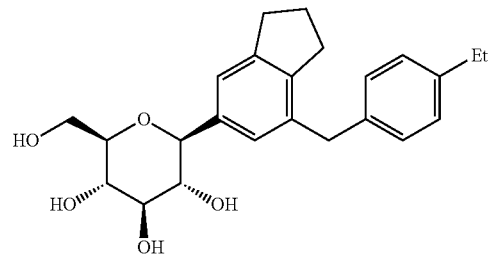 [SMILES: CCc1ccc(Cc2cc([C@@H]3O[C@H](CO)[C@@H](O)[C@H](O)[C@H]3O)cc3c2CCC3)cc1]

$^1$H NMR spectra (300 MHz, MeOD) δ 7.17 (s, 1H), 7.06-7.03 (m, 5H), 4.11 (d, 1H), 3.90-3.87 (m, 2H), 3.90-3.87 (m, 1H), 3.46-3.36 (m, 5H), 2.87 (t, 2H), 2.74 (t, 2H), 2.59 (q, 2H), 2.03 (t, 2H), 1.19 (t, 3H)
MS (ESI$^+$, m/z): [M + NH$_4$]$^+$ m/z 416.2434

| | |
|---|---|
| 17 | (2R,3S,4R,5R,6S)-2-(hydroxymethyl)-6-(7-(4-propylbenzyl)-2,3-dihydro-1H-inden-5-yl)tetrahydro-2H-pyran-3,4,5-triol |

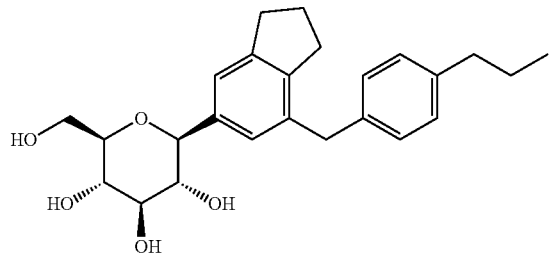 [SMILES: CCCc1ccc(Cc2cc([C@@H]3O[C@H](CO)[C@@H](O)[C@H](O)[C@H]3O)cc3c2CCC3)cc1]

$^1$H NMR spectra (300 MHz, MeOD) δ 7.12 (s, 1H), 6.98-6.94 (m, 5H), 4.03 (d, 2H), 3.82 (s, 2H), 3.72-3.55 (m, 4H), 3.23 (m, 1H), 2.77 (t, 2H), 2.64 (t, 2H), 2.47 (t, 2H), 1.92 (m, 2H), 1.52 (m, 2H), 0.88 (t, 3H)
MS (ESI$^+$, m/z): [M + NH$_4$]$^+$ m/z 430.2593

TABLE 2-continued

| Example | Compound name/Structural formula/Analysis data |
|---|---|
| 18 | (2R,3S,4R,5R,6S)-2-(hydroxymethyl)-6-(7-(4-isopropylbenzyl)-2,3-dihydro-1H-inden-5-yl)tetrahydro-2H-pyran-3,4,5-triol |

$^1$H NMR spectra (300 MHz, MeOD) δ 7.13 (s, 1H), 7.07-6.96 (m, 5H), 4.12-4.10 (d, 1H), 3.83-3.53 (m, 6H), 3.32-3.29 (m, 2H), 2.80 (m, 3H), 2.66 (t, 2H), 1.94 (t, 2H), 1.09 (d, 6H)
MS (ESI$^+$, m/z): [M + NH$_4$]$^+$ m/z 430.2591

| 19 | (2S,3R,4R,5S,6R)-2-(7-benzyl-2,3-dihydro-1H-inden-5-yl)-6-(hydroxymethyl)tetrahydro-2H-pyran-3,4,5-triol |

$^1$H NMR spectra (300 MHz, CDCl$_3$): δ 7.23-7.18 (m, 2H), 7.14-7.08 (m, 4H), 6.93 (s, 1H), 4.54 (br, 1H), 4.32 (br, 1H), 4.06 (d, 1H), 3.88 (s, 2H), 3.80-3.48 (m, 6H), 3.35-3.32 (m, 1H), 3.09 (br, 1H), 2.84 (t, 2H), 2.70 (t, 2H), 2.01-1.92 (m, 2H)
MS (ESI$^+$, m/z): [M + NH$_4$]$^+$ m/z 388.2127

| 20 | (2S,3R,4R,5S,6R)-2-(7-(4-ethoxy-3-fluorobenzyl)-2,3-dihydro-1H-inden-5-yl)-6-(hydroxymethyl)tetrahydro-2H-pyran-3,4,5-triol |

$^1$H NMR spectra (300 MHz, CDCl$_3$) δ 7.13 (s, 1H), 6.91 (s, 1H), 6.80-6.73 (m, 3H), 4.93 (br, 1H), 4.68 (br, 1H), 4.07-3.95 (m, 3H), 3.77-3.50 (m, 6H), 3.44 (m, 1H), 3.34 (d, 1H), 2.94 (br, 1H), 2.81 (t, 2H), 2.65 (t, 2H), 2.21 (br, 1H), 1.94 (t, 2H), 1.36 (t, 3H)
MS (ESI$^+$, m/z): [M + NH$_4$]$^+$ m/z 450.2288

TABLE 2-continued

| Example | Compound name/Structural formula/Analysis data |
|---|---|
| 21 | (2S,3R,4R,5S,6R)-2-(7-(4-ethoxy-2-fluorobenzyl)-2,3-dihydro-1H-inden-5-yl)-6-(hydroxymethyl)tetrahydro-2H-pyran-3,4,5-triol 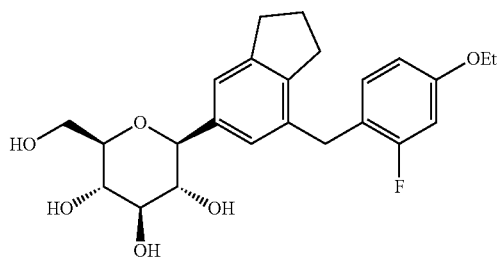 [SMILES: CCOc1ccc(Cc2cc([C@@H]3O[C@H](CO)[C@@H](O)[C@H](O)[C@H]3O)cc3c2CCC3)c(F)c1]  $^1$H NMR spectra (300 MHz, CDCl$_3$) δ 7.11 (s, 1H), 6.92 (s, 1H), 6.78 (t, 1H), 6.54-6.46 (m 2 H), 4.00 (s, 1H), 3.89-3.68 (m, 8H), 3.26-3.14 (m, 2H), 2.77 (t, 2H), 2.66 (t, 2H), 1.91 (t, 2H), 1.31 (t, 3H)  MS (ESI$^+$, m/z): [M + NH$_4$]$^+$ m/z 450.2294 |
| 22 | (2R,3S,4R,5R,6S)-2-(hydroxymethyl)-6-(7-(4-(trifluoromethoxy)benzyl)-2,3-dihydro-1H-inden-5-yl)tetrahydro-2H-pyran-3,4,5-triol 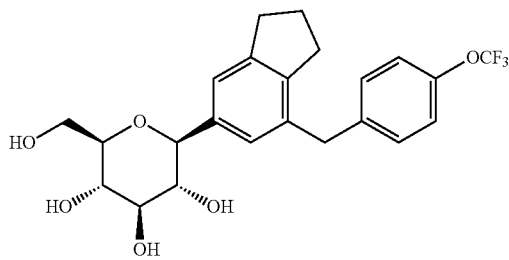 [SMILES: OC[C@H]1O[C@@H](c2cc3c(c(Cc4ccc(OC(F)(F)F)cc4)c2)CCC3)[C@H](O)[C@@H](O)[C@@H]1O]  $^1$H NMR spectra (300 MHz, CDCl$_3$) δ 7.34-7.05 (m, 5H), 6.99 (s, 1H), 4.08 (d, 1H), 3.97 (s, 2H), 3.89 (d, 1H), 3.72-3.70 (m, 1H), 3.49-3.39 (m, 4H), 2.88 (t, 2H), 2.70 (t, 2H), 1.99 (t, 2H)  MS (ESI$^+$, m/z): [M + NH$_4$]$^+$ m/z 472.1949 |
| 23 | (2S,3R,4R,5S,6R)-2-(7-(4-ethoxy-2,6-dimethylbenzyl)-2,3-dihydro-1H-inden-5-yl)-6-(hydroxymethyl)tetrahydro-2H-pyran-3,4,5-triol 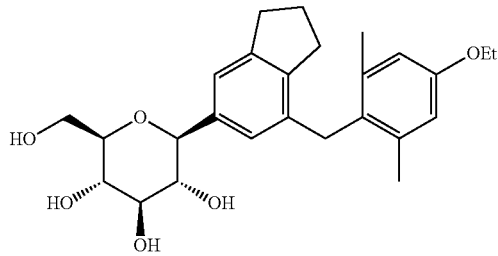 [SMILES: CCOc1cc(C)c(Cc2cc([C@@H]3O[C@H](CO)[C@@H](O)[C@H](O)[C@H]3O)cc3c2CCC3)c(C)c1]  $^1$H NMR spectra (300 MHz, CDCl$_3$) δ 7.11 (s, 1H), 6.63 (s, 2H), 6.35 (s, 1H), 4.03-3.95 (m, 3H), 3.83 (br, 3H), 3.63-3.58 (m, 2H), 3.44-3.87 (m, 2H), 2.96-2.88 (m, 4H), 2.18-2.12 (m, 8H), 1.41 (t, 3H)  MS (ESI$^+$, m/z): [M + NH$_4$]$^+$ m/z 460.2695 |

TABLE 2-continued

| Example | Compound name/Structural formula/Analysis data |
| --- | --- |
| 24 | (2R,3S,4R,5R,6S)-2-(hydroxymethyl)-6-(7-(4-(trifluoromethyl)benzyl)-2,3-dihydro-1H-inden-5-yl)tetrahydro-2H-pyran-3,4,5-triol 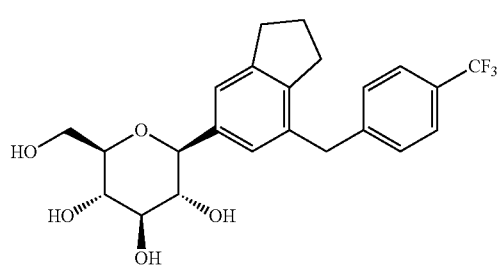 $^1$H NMR spectra (300 MHz, CDCl$_3$): δ 7.48 (d, 2H), 7.22-7.13 (m, 3H), 6.94 (s, 1H), 4.12 (d, 1H), 3.95 (s, 2H), 3.84-3.44 (m, 7H), 2.87 (t, 2H), 2.69 (t, 2H), 2.03 (q, 2H) MS (ESI$^+$, m/z): [M + NH$_4$]$^+$ m/z 456.2000 |
| 25 | (2S,3R,4R,5S,6R)-2-(7-(3-fluoro-4-methylbenzyl)-2,3-dihydro-1H-inden-5-yl)-6-(hydroxymethyl)tetrahydro-2H-pyran-3,4,5-triol 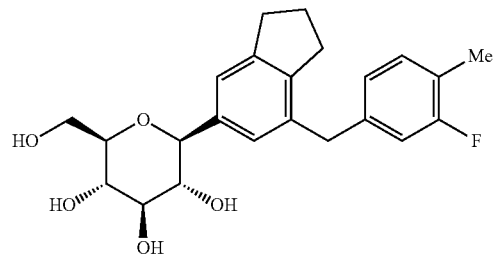 [SMILES: Cc1ccc(Cc2cc([C@@H]3O[C@H](CO)[C@@H](O)[C@H](O)[C@H]3O)cc3c2CCC3)cc1F] $^1$H NMR spectra (300 MHz, CDCl$_3$): δ 7.14 (s, 1H), 7.02 (t, 1H), 6.87 (s, 1H), 6.79-6.71 (m, 2H), 4.11 (t, 1H), 4.00 (s, 1H), 3.85 (s, 4H), 3.70-3.61 (m, 2H), 3.55 (d, 1H), 3.41 (t, 1H), 2.86 (t, 2H), 2.70 (t, 2H), 2.19 (s, 3H), 2.00 (q, 2H) MS (ESI$^+$, m/z): [M + NH$_4$]$^+$ m/z 420.2188 |
| 26 | (2S,3R,4R,5S,6R)-2-(7-(2-fluoro-4-methylbenzyl)-2,3-dihydro-1H-inden-5-yl)-6-(hydroxymethyl)tetrahydro-2H-pyran-3,4,5-triol 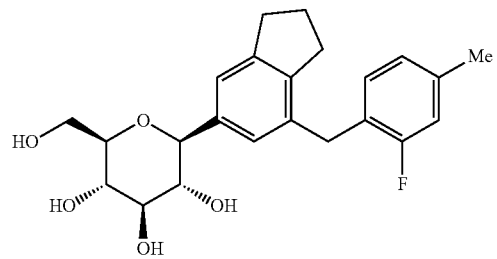 [SMILES: Cc1ccc(Cc2cc([C@@H]3O[C@H](CO)[C@@H](O)[C@H](O)[C@H]3O)cc3c2CCC3)c(F)c1] $^1$H NMR spectra (300 MHz, CDCl$_3$): δ 7.08 (s, 1H), 6.93-6.76 (m, 4H), 4.16-4.06 (m, 2H), 3.97-3.81 (m, 4H), 3.70-3.61 (m, 2H), 3.53 (d, 1H), 3.40 (t, 1H), 2.85 (t, 2H), 2.74 (t, 2H), 2.26 (s, 3H), 2.00 (q, 2H) MS (ESI$^+$, m/z): [M + NH$_4$]$^+$ m/z 420.2193 |

TABLE 2-continued

| Example | Compound name/Structural formula/Analysis data |
| --- | --- |
| 27 | (2S,3R,4R,5S,6R)-2-(7-(3,4-dimethoxybenzyl)-2,3-dihydro-1H-inden-5-yl)-6-(hydroxymethyl)tetrahydro-2H-pyran-3,4,5-triol<br><br>$^1$H NMR spectra (300 MHz, CDCl$_3$): δ 7.15 (s, 1H), 6.93 (s, 1H), 6.76 (d, 1H), 6.69-6.63 (m, 2H), 4.13 (d, 1H), 3.88-3.81 (m, 10H), 3.73-3.63 (m, 2H), 3.56-3.48 (m, 2H), 2.91 (t, 2H), 2.78 (t, 2H), 2.05 (q, 2H)<br>MS (ESI$^+$, m/z): [M + NH4]$^+$ m/z 448.2331 |
| 28 | (2S,3R,4R,5S,6R)-2-(7-(4-ethyl-3-fluorobenzyl)-2,3-dihydro-1H-inden-5-yl)-6-(hydroxymethyl)tetrahydro-2H-pyran-3,4,5-triol<br><br>$^1$H NMR spectra (300 MHz, CDCl$_3$) δ 7.19 (s, 1H), 7.13-7.06 (m, 2H), 6.88 (d, 1H), 6.77 (d, 1 H), 4.11 (d, 1H), 4.08 (d, 1H), 3.72-3.32 (m, 6H), 2.89 (t, 2H), 2.74 (t, 2H), 2.57 (t, 2H), 1.99 (t, 2H), 1.19 (t, 3H)<br>MS (ESI$^+$, m/z): [M + NH$_4$]$^+$ m/z 434.2334 |
| 29 | (2S,3R,4R,5S,6R)-2-(7-(benzo[d][1,3]dioxol-5-ylmethyl)-2,3-dihydro-1H-inden-5-yl)-6-(hydroxymethyl)tetrahydro-2H-pyran-3,4,5-triol<br><br>$^1$H NMR spectra (300 MHz, CDCl$_3$): δ 7.12 (s, 1H), 6.92 (s, 1H), 6.68-6.65 (m, 1H), 6.58-6.56 (m, 1H), 5.82 (s, 2H), 4.09-4.06 (m, 1H), 3.84-3.74 (m, 4H), 3.67-3.52 (m, 3H), 3.40-3.47 (m, 1H), 2.85 (t, 2H), 2.72 (t, 2H), 2.01-1.96 (m, 2H) MS (ESI$^+$, m/z): [M + NH$_4$]$^+$ m/z 432.2028 |

TABLE 2-continued

| Example | Compound name/Structural formula/Analysis data |
| --- | --- |
| 30 | (2S,3R,4R,5S,6R)-2-(7-((2,3-dihydrobenzo[1,4]dioxin-6-yl)methyl)-2,3-dihydro-1H-inden-5-yl)-6-(hydroxymethyl)tetrahydro-2H-pyran-3,4,5-triol 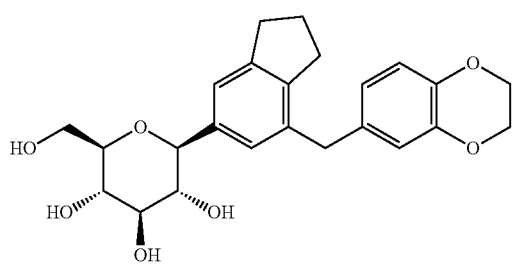 $^1$H NMR spectra (300 MHz, CDCl$_3$) δ 7.17 (s, 1H), 7.02 (s, 1H), 6.71-6.59 (m, 3H), 4.17 (s, 4H), 4.10 (d, 1H), 3.90-3.67 (m, 4H), 3.46-3.33 (m, 4H), 2.89 (t, 2H), 2.74 (t, 2H), 1.99 (t, 2H)<br>MS (ESI$^+$, m/z): [M + NH$_4$]$^+$ m/z 446.2184 |
| 31 | (2S,3R,4R,5S,6R)-2-(7-(4-(tert-butyl)benzyl)-2,3-dihydro-1H-inden-5-yl)-6-(hydroxymethyl)tetrahydro-2H-pyran-3,4,5-triol 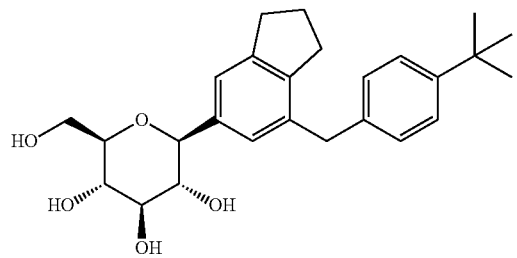 [SMILES: CC(C)(C)c1ccc(Cc2cc([C@@H]3O[C@H](CO)[C@@H](O)[C@H](O)[C@H]3O)cc3c2CCC3)cc1] $^1$H NMR spectra (300 MHz, CDCl$_3$): δ 7.25-7.19 (m, 2H), 7.12 (s, 1H), 7.02-6.96 (m, 3H), 4.13-4.06 (m, 2H), 3.83-3.32 (m, 7H), 2.81 (t, 2H), 2.69 (t, 2H), 1.84 (m, 2H), 1.24 (s, 9H).<br>MS (ESI$^+$, m/z): [M + NH4]$^+$ m/z 444.2749 |
| 32 | (2S,3R,4R,5S,6R)-2-(7-(3,4-dimethylbenzyl)-2,3-dihydro-1H-inden-5-yl)-6-(hydroxymethyl)tetrahydro-2H-pyran-3,4,5-triol 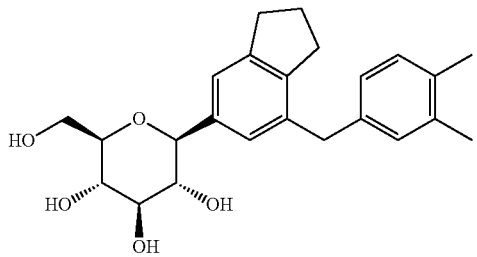 [SMILES: Cc1ccc(Cc2cc([C@@H]3O[C@H](CO)[C@@H](O)[C@H](O)[C@H]3O)cc3c2CCC3)cc1C] $^1$H NMR spectra (300 MHz, CDCl$_3$): δ 7.13 (s, 1H), 7.00-6.74 (m, 4H), 4.10 (d, 1H), 3.90-3.48 (m, 8H), 2.87 (t, 2H), 2.76 (t, 2H), 2.19 (t, 6H), 2.01 (t, 2H)<br>MS (ESI$^+$, m/z): [M + NH$_4$]$^+$ 416.2436 |

TABLE 2-continued

| Example | Compound name/Structural formula/Analysis data |
| --- | --- |
| 33 | (2R,3S,4R,5R,6S)-2-(hydroxymethyl)-6-(7-(3-methylbenzyl)-2,3-dihydro-1H-inden-5-yl)tetrahydro-2H-pyran-3,4,5-triol $^1$H NMR spectra (300 MHz, CDCl$_3$): δ 7.12-7.04 (m, 2H), 6.93-6.85 (m, 4H), 5.00 (br, 1H), 4.81 (br, 1H), 4.04 (d, 1H), 3.83 (s, 2H), 3.78-3.51 (m, 6H), 3.31 (d, 1H), 3.01 (br, 1H), 2.81 (t, 2H), 2.69 (t, 2H), 2.47 (br, 1H), 2.24 (s, 3H), 1.99-1.90 (m, 2H)
MS (ESI$^+$, m/z): [M + NH$_4$]$^+$ 402.2 |
| 34 | (2R,3S,4R,5R,6S)-2-(hydroxymethyl)-6-(7-(4-(2,2,2-trifluoroethoxy)benzyl)-2,3-dihydro-1H-inden-5-yl)tetrahydro-2H-pyran-3,4,5-triol $^1$H NMR spectra (300 MHz, CDCl$_3$): δ 7.13 (s, 1H), 7.04 (d, 2H), 6.91 (s, 1H), 6.80 (d, 2H), 4.25 (q, 2H), 4.09 (d, 1H), 3.85-3.79 (m, 4H), 3.66 (t, 2H), 3.54 (d, 1H), 3.40 (t, 1H), 2.86 (t, 2H), 2.70 (t, 2H), 1.99 (t, 2H)
MS (ESI$^+$, m/z): [M + NH$_4$]$^+$ 486.2103 |
| 35 | (2S,3R,4R,5S,6R)-2-(7-((2,2-dimethylbenzo[d][1,3]dioxol-5-yl)methyl)-2,3-dihydro-1H-inden-5-yl)-6-(hydroxymethyl)tetrahydro-2H-pyran-3,4,5-triol $^1$H NMR spectra (300 MHz, CDCl$_3$): δ 7.11 (s, 1H), 6.94 (s, 1H), 6.57-6.48 (m, 3H), 4.91-4.67 (br, 2H), 4.07 (d, 1H), 3.76-3.34 (m, 9H), 2.81 (t, 2H), 2.70 (t, 2H), 2.22 (br, 3H), 2.00-1.93 (m, 2H), 1.58 (s, 6H)
MS (ESI$^+$, m/z): [M + NH$_4$]$^+$ m/z 460.2352 |

EXAMPLE 36

Preparation of (2S,3R,4R,5S,6R)-2-(7-((5-(4-fluorophenyl)thiophen-2-yl)methyl)-2,3-dihydro-1H-inden-5-yl)-6-(hydroxymethyl)tetrahydro-2H-pyran-3,4,5-triol

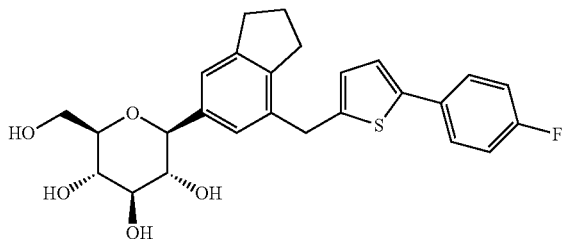 [SMILES: OC[C@H]1O[C@@H](c2cc3c(c(Cc4ccc(-c5ccc(F)cc5)s4)c2)CCC3)[C@H](O)[C@@H](O)[C@@H]1O]

The compound (2R,3R,4R,5S)-3,4,5-tris(benzyloxy)-2-((benzyloxy)methyl)-6-(7-((5-(4-fluorophenyl)thiophen-2-yl)methyl)-2,3-dihydro-1H-inden-5-yl)tetrahydro-2H-pyran (196 mg) synthesized in the same manner as in Step 1 and Step 2 of Example 13 was dissolved in dichloromethane (2.5 mL), and an argon atmosphere was substituted. Then, the reaction solution was cooled until the inner temperature reached −78° C., and a solution (1.3 mL) in which 1.0M boron trichloride was dissolved in dichloromethane was then slowly added thereto while stirring. The reaction solution was stirred at −78° C. for 30 minutes. After the reaction was completed, methanol was added, and the reaction solution was stirred, and then dried under reduced pressure. A sodium bicarbonate aqueous solution was added, and the reaction solution was then extracted with ethyl acetate. An organic layer was dried using anhydrous magnesium sulfate, and filtered under reduced pressure. The filtrate was dried under reduced pressure, and then purified by column chromatography to obtain a title compound (30 mg).

$^1$H NMR spectra (300 MHz, MeOD): δ 7.56-7.51 (m, 2H), 7.21-7.04 (m, 5H), 6.75 (m, 1H), 3.91 (d, 1H), 3.87-3.59 (m, 5H), 3.46-3.27 (m, 3H), 2.94-2.84 (m, 4H), 2.06 (t, 2H)

MS (ESI$^+$, m/z): [M+NH$_4$]$^+$ m/z 488.1917

The following compounds of Examples 37 to 40 were synthesized in the same synthetic pathway as in Example 36.

TABLE 3

| Example | Compound name/Structural formula/Analysis data |
|---|---|
| 37 | (2S,3R,4R,5S,6R)-2-(7-(benzo[b]thiophen-2-ylmethyl)-2,3-dihydro-1H-inden-5-yl)-6-(hydroxymethyl)tetrahydro-2H-pyran-3,4,5-triol |

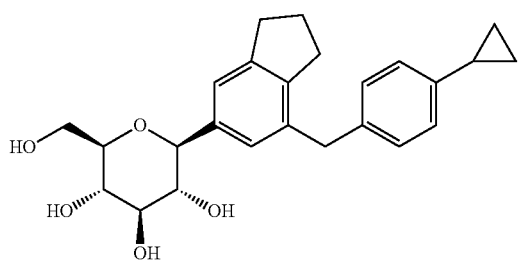 [SMILES: OC[C@H]1O[C@@H](c2cc3c(c(Cc4ccc(C5CC5)cc4)c2)CCC3)[C@H](O)[C@@H](O)[C@@H]1O]

$^1$H NMR spectra (300 MHz, CDCl$_3$): δ 7.68 (d, 1H), 7.60 (d, 1H), 7.35-7.18 (m, 3H), 7.05 (s, 1H), 6.91 (s, 1H), 4.13-4.10 (m, 3H), 3.83-3.40 (m, 8H), 2.91-2.80 (m, 4H), 2.57 (s, 1H), 2.40 (s, 1H), 2.02 (q, 2H)
MS (ESI$^+$, m/z): [M + NH$_4$]$^+$ m/z 444.1840

| 38 | (2S,3R,4R,5S,6R)-2-(7-(4-cyclopropylbenzyl)-2,3-dihydro-1H-inden-5-yl)-6-(hydroxymethyl)tetrahydro-2H-pyran-3,4,5-triol |

$^1$H NMR spectra (300 MHz, CDCl$_3$): δ 7.11 (s, 1H), 6.98-6.88 (m, 5H), 4.02 (d, 1H), 3.82-3.32 (m, 8H), 2.81 (t, 2H), 2.65 (t, 2H), 1.92 (m, 2H), 1.78 (m, 1H), 0.85 (m, 2H), 0.58 (m, 2H).
MS (ESI+, m/z): [M + NH$_4$]$^+$ m/z 428.2434

TABLE 3-continued

| Example | Compound name/Structural formula/Analysis data |
|---|---|
| 39 | (2S,3R,4R,5S,6R)-2-(7-(4-cyclopropyl-2-fluorobenzyl)-2,3-dihydro-1H-inden-5-yl)-6-(hydroxymethyl)tetrahydro-2H-pyran-3,4,5-triol |

$^1$H NMR spectra (300 MHz, CDCl$_3$): δ 7.16 (s, 1H), 7.01-6.93 (m, 1H), 6.80 (t, 1H), 6.64-6.61 (m, 2H), 4.04 (d, 1H), 3.98-3.26 (m, 8H), 2.77 (t, 2H), 2.64 (t, 2H), 1.90 (m, 2H), 1.72 (m, 1H), 0.84 (m, 2H), 0.55 (m, 2H).
MS (ESI$^+$, m/z): [M + NH$_4$]$^+$ m/z 446.2342

| 40 | (2S,3R,4R,5S,6R)-2-(7-(4-chlorobenzyl)-2,3-dihydro-1H-inden-5-yl)-6-(hydroxymethyl)tetrahydro-2H-pyran-3,4,5-triol |

$^1$H NMR spectra (300 MHz, MeOD): δ 7.25-7.12 (m, 5H), 7.04 (s, 1H), 4.11 (d, 1H), 3.87 (d, 1H), 3.71 (m, 1H), 3.45-3.32 (m, 6H), 2.89 (t, 2H), 2.70 (t, 2H), 1.99 (m, 2H).
MS (ESI$^+$, m/z): [M + NH$_4$]$^+$ 422.1726

The above-described compounds prepared in the Examples were evaluated, as follows.

EXPERIMENTAL EXAMPLE 1

[$^{14}$C]-AMG Uptake Assay

For the evaluation of the pharmaceutical efficacies of the compounds as a SGLT inhibitor, a glucose uptake assay was conducted by using stable cell lines, i.e., HEK293-hSGLT1 and HEK293-hSGLT2. The stable cell lines were prepared by transfection of human embryonic kidney 293 (HEK293) cell line with pcDNA3.1(+)-FLAG-hSGLT1 and pcDNA3.1(+)-FLAG-hSGLT2 vectors.

The cells were seeded in a 96-well poly-D-lysine (PDL) coated plate at a density of 2.5×10$^4$ cells/well and cultured in a cell culture incubator for one day at 37° C., 5% CO$_2$. Then, the cells were washed once with 1× assay buffer (140 mM NaCl, 5 mM KCl, 2.5 mM CaCl$_2$, 1 mM MgSO$_4$.7H$_2$O, 1 mM KH$_2$PO$_4$, 10 mM HEPES) and pre-incubated in a cell culture incubator for 30 minutes with 1× assay buffer at 37° C., 5% CO$_2$. Each compound obtained in the Examples was 10-fold diluted with 1× assay buffer. The diluted compounds were added to the plate at various concentrations and then cultured in a cell culture incubator for 1 hour at 37° C., 5% CO$_2$.

Radioactive [$^{14}$C]-alpha-methyl-D-glucopyranoside (Cat# NEC659250UC, Perkin Elmer) was diluted with 1× assay buffer at a concentration of 0.2 μCi. The diluted [$^{14}$C]-AMG was added to all the wells in plate in the same amount, and the cells were cultured in a cell culture incubator for 2 hours at 37° C., 5% CO$_2$. The cells were washed three times with cold Dulbecco's Phosphate buffer saline (DPBS) and then lysed with 0.2 N NaOH for 10 minutes at room temperature with shaking. After addition of MicroScint 20 fluid, the cells were allowed to shake for 15 minutes at room temperature, and then the activity of [$^{14}$C]AMG was quantified on a β-scintillation counter. IC$_{50}$ of each of the compounds was determined by GraphPad Prism 4.0 software.

The results are summarized in Table 4 below.

TABLE 4

| | IC$_{50}$ [nM] | |
|---|---|---|
| Compound | hSGLT1 | hSGLT2 |
| Example 14 | 31.9 | 4.0 |
| Example 15 | 7.7 | 9.6 |
| Example 16 | 54.6 | 5.6 |
| Example 22 | 510.5 | 9.2 |
| Example 24 | 267.1 | 6.8 |
| Example 29 | 35.2 | 3.5 |
| Example 30 | 55.2 | 3.5 |
| Example 31 | 177.5 | 5.8 |
| Example 32 | 63.2 | 4.5 |
| Example 34 | 553.1 | 13.5 |
| Example 36 | 84.9 | 9.0 |
| Example 37 | 19.8 | 9.0 |

TABLE 4-continued

| Compound | IC$_{50}$ [nM] | |
|---|---|---|
| | hSGLT1 | hSGLT2 |
| Example 38 | 24.9 | 5.8 |
| Example 40 | 209.9 | 28.8 |

As shown in Table 4, the compounds of the Examples according to the present invention have a great inhibitory activity against SGLTs.

EXPERIMENTAL EXAMPLE 2

Oral Glucose Tolerance Test (oGTT)

The pharmaceutical efficacy of the compound prepared in Example 1 was investigated by an oral glucose tolerance test using C57BL/6 male mice (8-week-old, prepared and supplied from Orient Chemical Co. Ltd.).

A total of 6 mice were fasted for 16 hours, weighed, and then divided into three groups. Thereafter, the compound of Example 1, 5% 1-methyl-2-pyrrolidinone as a vehicle, a mixed solution of 20% PEG and 75% 20 mM sodium diphophate, and canagliflozin also known as a SGLT2 inhibitor (a control) were orally administered to the mice in each group at a dose of 10 mg/kg. After 30 minutes, 2 g/kg of glucose was orally administered to the mice in all the groups. Thereafter, the distal caudal veins of tails of the test mice were slightly injured, and blood was gathered at time points of −2, 0, 0.25, 0.5, 1 and 2 hours after the oral administration of glucose. Then, blood glucose was measured using a OneTouch blood glucose meter (OneTouch Ultra, Lifescan, Inc., USA).

Figure 2:
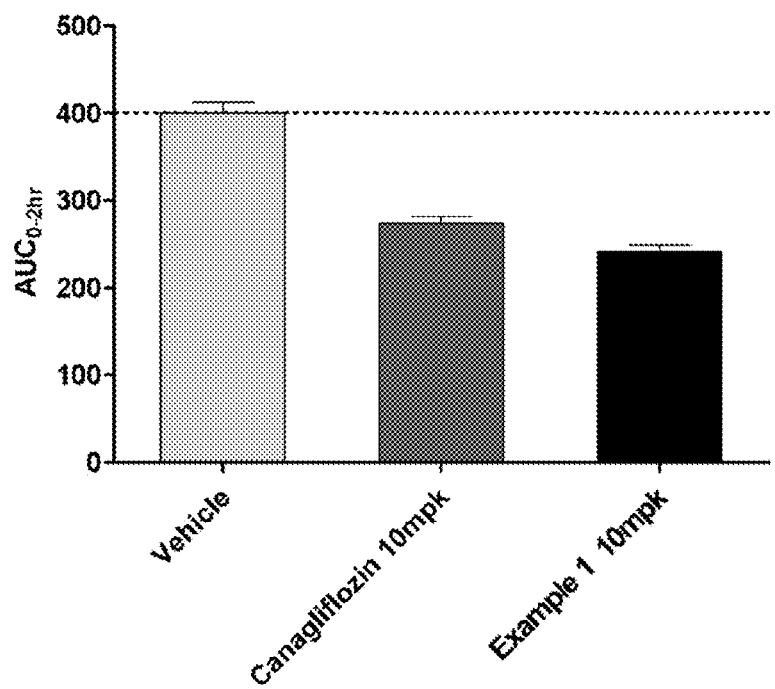
FIG. 2: a graph illustrating an area under curve (AUC) at a time interval from 0 to 2 hours after the compound of Example 1, 5% 1-methyl-2-pyrrolidinone as a vehicle, a mixed solution of 20% PEG and 75% 20 mM sodium diphophate, and canagliflozin as a control are orally administered to the mice.

The results are shown in FIGS. 1 and 2. FIG. 1 is a graph showing the blood glucose concentrations depending on time, and FIG. 2 is a graph showing an area under curve (AUC) at a time interval from 0 to 2 hours.

As shown in FIGS. 1 and 2, it was revealed that the compound of Formula 1 according to one exemplary embodiment of the present invention has a superior blood glucose lowering effect, compared to the representative SGLT2 inhibitor, canagliflozin.

EXPERIMENTAL EXAMPLE 3

Urinary Glucose Excretion Test (UGE Test)

The pharmaceutical efficacies of the compounds prepared in the Examples were investigated by a urinary glucose excretion test using C57BL/6 male mice (8-week-old, prepared and supplied from Orient Chemical Co. Ltd.).

Two mice were used in each group. The mice were fasted for 16 hours, and the compound of each of the Examples [10 mg/kg of the compound of Examples 1 to 12; and 3 mg/kg of the compound of Examples 13 to 38] was dissolved in a vehicle [a mixed solution of 5% 1-methyl-2-pyrrolidinone, 20% PEG, and 75% 20 mM sodium diphosphate], and orally administered to the mice. After 30 minutes, 2 g/kg of glucose was orally administered to the mice in all the groups. Thereafter, the mice were immediately put into a metabolic cage, and urine was collected for 24 hours. The mice were freely fed an hour after the administration of glucose.

The results obtained from the test, that is, the results obtained by measuring urinary glucose excretion in the C57BL/6 male mice according to the compounds of the Examples, are listed in Table 5.

TABLE 5

| Compound | UGE (mg/20 g/24 hr) |
|---|---|
| Example 1 | 1.2 |
| Example 2 | 8.3 |
| Example 3 | 3.7 |
| Example 4 | 4.6 |
| Example 5 | 3.7 |
| Example 6 | 3.9 |
| Example 7 | 2.8 |
| Example 8 | 4.3 |
| Example 9 | 4.6 |
| Example 10 | 3.2 |
| Example 11 | 3.0 |
| Example 12 | 0 |
| Example 13 | 1.7 |
| Example 15 | 8.1 |
| Example 16 | 16.4 |
| Example 17 | 1.0 |
| Example 18 | 7.0 |
| Example 20 | 0.6 |
| Example 21 | 4.2 |
| Example 22 | 9.6 |
| Example 25 | 5.5 |
| Example 26 | 4.8 |
| Example 30 | 7.2 |
| Example 37 | 14.5 |
| Example 38 | 14.8 |

As shown in Table 5, the compounds of the Examples according to the present invention have a significant therapeutic effect for diabetes.

What is claimed is:

1. A bicyclic derivative represented by Formula 1, or a pharmaceutically acceptable salt, isomer, hydrate or solvate thereof:

[Formula 1]

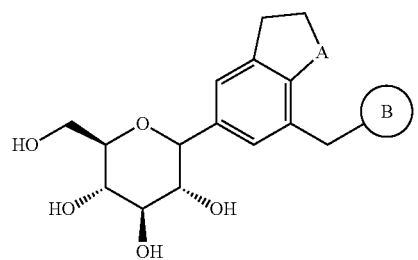

wherein

A is —O— or —CH$_2$—;

the ring B is selected from the group consisting of the following Structural Formulae (i), (ii) and (iii):

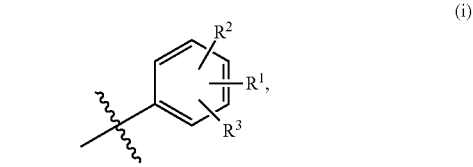

(i)

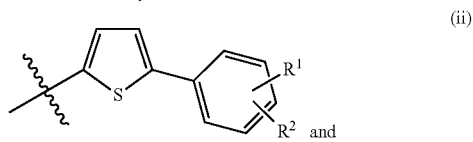

(ii)

and

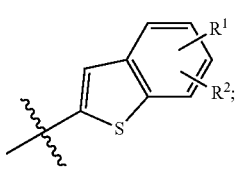

(iii)

R¹, R², and R³ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 5 fluoro groups, $C_{1-4}$ alkyl, $C_{3-6}$ cycloalkyl, $C_{1-8}$ alkoxy, 3- to 6-membered heterocycloalkyloxy, or $C_{1-3}$ alkylsulfonyl groups, wherein the $C_{1-8}$ alkoxy may be substituted with one to two $C_{1-8}$ alkoxy or $C_{3-6}$ cycloalkyloxy groups;

R¹ and R² substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—R⁴)—, and unreplaced methylene groups may be each independently substituted with 1 to 4 halogens or methyl groups;

R⁴ is H or benzyl; and the heterocycloalkyl includes at least one heteroatom selected from the group consisting of O, N, and S.

2. The compound of claim 1, wherein the ring B is represented by Structural Formula (i);

R¹, R², and R³ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 3 fluoro groups, $C_{1-4}$ alkyl, $C_{3-6}$ cycloalkyl, $C_{1-8}$ alkoxy, 3- to 6-membered heterocycloalkyloxy, or methylsulfonyl groups, wherein the $C_{1-8}$ alkoxy may be substituted with one to two $C_{1-8}$ alkoxy or $C_{3-6}$ cycloalkyloxy groups;

R¹ and R² substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—R⁴)—, and unreplaced methylene groups may be each independently substituted with one to two fluoro groups or methyl groups;

R⁴ is H or benzyl; and the heterocycloalkyl includes at least one heteroatom selected from the group consisting of O, N, and S.

3. The compound of claim 1, wherein the ring B is represented by Structural Formula (ii) or (iii); and R¹ and R² each independently are H, halogen, hydroxy, or $C_{1-8}$ alkyl.

4. The compound of claim 1, wherein A is —O—.

5. The compound of claim 4, wherein the ring B is represented by Structural Formula (i);

R¹, R², and R³ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{2-7}$ alkenyl, $C_{2-7}$ alkynyl, $C_{3-6}$ cycloalkyl, $C_{1-8}$ alkoxy, and $C_{3-6}$ cycloalkyloxy may be each independently substituted with 1 to 3 fluoro groups, $C_{1-4}$ alkyl, $C_{3-6}$ cycloalkyl, $C_{1-8}$ alkoxy, 3- to 6-membered heterocycloalkyloxy, or methylsulfonyl groups, wherein the $C_{1-8}$ alkoxy may be substituted with one to two $C_{1-8}$ alkoxy or $C_{3-6}$ cycloalkyloxy groups;

R¹ and R² substituted at two adjacent carbon atoms may be joined together to form $C_{3-5}$ alkylene bridge, where one to two methylene groups in the $C_{3-5}$ alkylene bridge may be each independently replaced with —O—, —S—, —S(=O)—, —S(=O)$_2$—, —C(=O)—, or —N(—R⁴)—, and unreplaced methylene groups may be each independently substituted with one to two fluoro groups or methyl groups;

R⁴ is H or benzyl; and the heterocycloalkyl includes at least one heteroatom selected from the group consisting of O, N, and S.

6. The compound of claim 1, wherein

A is —CH$_2$—;

R¹, R², and R³ each independently are H, halogen, hydroxy, $C_{1-8}$ alkyl, $C_{2-7}$ alkenyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{3-6}$ cycloalkyl, $C_{1-8}$ alkoxy, and $C_{3-6}$ cycloalkyloxy may be each independently substituted with 1 to 5 fluoro groups, $C_{1-8}$ alkyl, $C_{3-6}$ cycloalkyl, or $C_{1-8}$ alkoxy groups; and R¹ and R² substituted at two adjacent carbon atoms may be joined together to form $C_{3-5}$ alkylene bridge, where one to two methylene groups in the $C_{3-5}$ alkylene bridge may be replaced with an oxygen atom, and methylene groups which are not replaced with oxygen atom may be each independently substituted with one to two fluoro or methyl groups.

7. The compound of claim 6, wherein the ring B is represented by Structural Formula (i);

R¹, R², and R³ each independently are H, halogen, hydroxy, $C_{1-8}$ alkyl, $C_{2-7}$ alkynyl, $C_{3-6}$ cycloalkyl, $C_{1-8}$ alkoxy, or $C_{3-6}$ cycloalkyloxy, wherein the $C_{1-8}$ alkyl, $C_{3-6}$ cycloalkyl, $C_{1-8}$ alkoxy, and $C_{3-6}$ cycloalkyloxy may be each independently substituted with 1 to 3 fluoro groups, $C_{1-8}$ alkyl, $C_{3-6}$ cycloalkyl, or $C_{1-8}$ alkoxy groups; and R¹ and R² substituted at two adjacent carbon atoms may be joined together to form $C_{3-5}$ alkylene bridge, where one to two methylene groups in the $C_{3-5}$ alkylene bridge may be replaced with an oxygen atom, and methylene groups which are not replaced with oxygen atoms may be each independently substituted with one to two fluoro or methyl groups.

8. The compound of claim 6, wherein the ring B is represented Structural Formula (i);

R¹, R², and R³ each independently are H, a fluoro group, a chloro group, a hydroxy, $C_{1-6}$ alkyl, $C_{3-6}$ cycloalkyl, or $C_{1-6}$ alkoxy, wherein the $C_{1-6}$ alkyl and $C_{1-6}$ alkoxy may be each independently substituted with 1 to 3 $C_{1-6}$ alkyl or fluoro groups; and R¹ and R² substituted at two adjacent carbon atoms may be joined together to form —O—(R⁴)$_n$—O— (wherein n is 1 or 2, and R⁴ each independently is —CH$_2$—, —CH(CH$_3$)—, or —C(CH$_3$)$_2$—).

9. The compound of claim 1, which is selected from the group consisting of:

1) (2S,3R,4R,5S,6R)-2-(7-(4-ethoxybenzyl)-2,3-dihydrobenzofuran-5-yl)-6-hydroxymethyl-tetrahydro-2H-pyran-3,4,5-triol;

2) (2S,3R,4R,5S,6R)-2-(7-(4-ethylbenzyl)-2,3-dihydrobenzofuran-5-yl)-6-hydroxymethyl-tetrahydro-2H-pyran-3,4,5-triol;
3) (2R,3S,4R,5R,6S)-2-hydroxymethyl-6-(7-(4-n-propylbenzyl)-2,3-dihydrobenzofuran-5-yl)-tetrahydro-2H-pyran-3,4,5-triol;
4) (2R,3S,4R,5R,6S)-2-hydroxymethyl-6-(7-(4-trifluoromethylbenzyl)-2,3-dihydrobenzofuran-5-yl)tetrahydro-2H-pyran-3,4,5-triol;
5) (2R,3S,4R,5R,6S)-2-hydroxymethyl-6-(7-(4-trifluoromethoxybenzyl)-2,3-dihydrobenzofuran-5-yl)tetrahydro-2H-pyran-3,4,5-triol;
6) (2S,3R,4R,5S,6R)-2-(7-(4-fluorobenzyl)-2,3-dihydrobenzofuran-5-yl)-6-(hydroxymethyl)tetrahydro-2H-pyran-3,4,5-triol;
7) (2S,3R,4R,5S,6R)-2-(7-((2,3-dihydrobenzo[b][1,4]dioxin-6-yl)methyl)-2,3-dihydrobenzofuran-5-yl)-6-(hydroxymethyl)tetrahydro-2H-pyran-3,4,5-triol;
8) (2S,3R,4R,5S,6R)-2-(7-(4-(cyclopropylmethoxy)benzyl)-2,3-dihydrobenzofuran-5-yl)-6-(hydroxymethyl)tetrahydro-2H-pyran-3,4,5-triol;
9) (2S,3R,4R,5S,6R)-2-(7-(4-ethoxy-3-fluorobenzyl)-2,3-dihydrobenzofuran-5-yl)-6-(hydroxymethyl)tetrahydro-2H-pyran-3,4,5-triol;
10) (2S,3R,4R,5S,6R)-2-(7-(4-ethoxy-2-fluorobenzyl)-2,3-dihydrobenzofuran-5-yl)-6-(hydroxymethyl)tetrahydro-2H-pyran-3,4,5-triol;
11) (2S,3R,4R,5S,6R)-2-(7-(4-hydroxybenzyl)-2,3-dihydrobenzofuran-5-yl)-6-(hydroxymethyl)tetrahydro-2H-pyran-3,4,5-triol;
12) (2S,3S,4R,5R,6S)-2-(hydroxymethyl)-6-(7-(4-(3-(methylsulfonyl)propoxy)benzyl)-2,3-dihydrofuran-5-yl)tetrahydro-2H-pyran-3,4,5-triol;
13) (2S,3R,4R,5S,6R)-2-(7-(4-ethoxybenzyl)-2,3-dihydro-1H-inden-5-yl)-6-(hydroxymethyl)tetrahydro-2H-pyran-3,4,5-triol;
14) (2R,3S,4R,5R,6S)-2-(hydroxymethyl)-6-(7-(4-methoxybenzyl)-2,3-dihydro-1H-inden-5-yl)tetrahydro-2H-pyran-3,4,5-triol;
15) (2R,3S,4R,5R,6S)-2-(hydroxymethyl)-6-(7-(4-methylbenzyl)-2,3-dihydro-1H-inden-5-yl)tetrahydro-2H-pyran-3,4,5-triol;
16) (2S,3R,4R,5S,6R)-2-(7-(4-ethylbenzyl)-2,3-dihydro-1H-inden-5-yl)-6-(hydroxymethyl)tetrahydro-2H-pyran-3,4,5-triol;
17) (2R,3S,4R,5R,6S)-2-(hydroxymethyl)-6-(7-(4-propylbenzyl)-2,3-dihydro-1H-inden-5-yl)tetrahydro-2H-pyran-3,4,5-triol;
18) (2R,3S,4R,5R,6S)-2-(hydroxymethyl)-6-(7-(4-isopropylbenzyl)-2,3-dihydro-1H-inden-5-yl)tetrahydro-2H-pyran-3,4,5-triol;
19) (2S,3R,4R,5S,6R)-2-(7-benzyl-2,3-dihydro-1H-inden-5-yl)-6-(hydroxymethyl)tetrahydro-2H-pyran-3,4,5-triol;
20) (2S,3R,4R,5S,6R)-2-(7-(4-ethoxy-3-fluorobenzyl)-2,3-dihydro-1H-inden-5-yl)-6-(hydroxymethyl)tetrahydro-2H-pyran-3,4,5-triol;
21) (2S,3R,4R,5S,6R)-2-(7-(4-ethoxy-2-fluorobenzyl)-2,3-dihydro-1H-inden-5-yl)-6-(hydroxymethyl)tetrahydro-2H-pyran-3,4,5-triol;
22) (2R,3S,4R,5R,6S)-2-(hydroxymethyl)-6-(7-(4-(trifluoromethoxy)benzyl)-2,3-dihydro-1H-inden-5-yl)tetrahydro-2H-pyran-3,4,5-triol;
23) (2S,3R,4R,5S,6R)-2-(7-(4-ethoxy-2,6-dimethylbenzyl)-2,3-dihydro-1H-inden-5-yl)-6-(hydroxymethyl)tetrahydro-2H-pyran-3,4,5-triol;
24) (2R,3S,4R,5R,6S)-2-(hydroxymethyl)-6-(7-(4-(trifluoromethyl)benzyl)-2,3-dihydro-1H-inden-5-yl)tetrahydro-2H-pyran-3,4,5-triol;
25) (2S,3R,4R,5S,6R)-2-(7-(3-fluoro-4-methylbenzyl)-2,3-dihydro-1H-inden-5-yl)-6-(hydroxymethyl)tetrahydro-2H-pyran-3,4,5-triol;
26) (2S,3R,4R,5S,6R)-2-(7-(2-fluoro-4-methylbenzyl)-2,3-dihydro-1H-inden-5-yl)-6-(hydroxymethyl)tetrahydro-2H-pyran-3,4,5-triol;
27) (2S,3R,4R,5S,6R)-2-(7-(3,4-dimethoxybenzyl)-2,3-dihydro-1H-inden-5-yl)-6-(hydroxymethyl)tetrahydro-2H-pyran-3,4,5-triol;
28) (2S,3R,4R,5S,6R)-2-(7-(4-ethyl-3-fluorobenzyl)-2,3-dihydro-1H-inden-5-yl)-6-(hydroxymethyl)tetrahydro-2H-pyran-3,4,5-triol;
29) (2S,3R,4R,5S,6R)-2-(7-(benzo[d][1,3]dioxol-5-ylmethyl)-2,3-dihydro-1H-inden-5-yl)-6-(hydroxymethyl)tetrahydro-2H-pyran-3,4,5-triol;
30) (2S,3R,4R,5S,6R)-2-(7-((2,3-dihydrobenzo[1,4]dioxin-6-yl)methyl)-2,3-dihydro-1H-inden-5-yl)-6-(hydroxymethyl)tetrahydro-2H-pyran-3,4,5-triol;
31) (2S,3R,4R,5S,6R)-2-(7-(4-(tert-butyl)benzyl)-2,3-dihydro-1H-inden-5-yl)-6-(hydroxymethyl)tetrahydro-2H-pyran-3,4,5-triol;
32) (2S,3R,4R,5S,6R)-2-(7-(3,4-dimethylbenzyl)-2,3-dihydro-1H-inden-5-yl)-6-(hydroxymethyl)tetrahydro-2H-pyran-3,4,5-triol;
33) (2R,3S,4R,5R,6S)-2-(hydroxymethyl)-6-(7-(3-methylbenzyl)-2,3-dihydro-1H-inden-5-yl)tetrahydro-2H-pyran-3,4,5-triol;
34) (2R,3S,4R,5R,6S)-2-(hydroxymethyl)-6-(7-(4-(2,2,2-trifluoroethoxy)benzyl)-2,3-dihydro-1H-inden-5-yl)tetrahydro-2H-pyran-3,4,5-triol;
35) (2S,3R,4R,5S,6R)-2-(7-((2,2-dimethylbenzo[d][1,3]dioxol-5-yl)methyl)-2,3-dihydro-1H-inden-5-yl)-6-(hydroxymethyl)tetrahydro-2H-pyran-3,4,5-triol;
36) (2S,3R,4R,5S,6R)-2-(7-((5-(4-fluorophenyl)thiophen-2-yl)methyl)-2,3-dihydro-1H-inden-5-yl)-6-(hydroxymethyl)tetrahydro-2H-pyran-3,4,5-triol;
37) (2S,3R,4R,5S,6R)-2-(7-(benzo[b]thiophen-2-ylmethyl)-2,3-dihydro-1H-inden-5-yl)-6-(hydroxymethyl)tetrahydro-2H-pyran-3,4,5-triol;
38) (2S,3R,4R,5S,6R)-2-(7-(4-cyclopropylbenzyl)-2,3-dihydro-1H-inden-5-yl)-6-(hydroxymethyl)tetrahydro-2H-pyran-3,4,5-triol;
39) (2S,3R,4R,5S,6R)-2-(7-(4-cyclopropyl-2-fluorobenzyl)-2,3-dihydro-1H-inden-5-yl)-6-(hydroxymethyl)tetrahydro-2H-pyran-3,4,5-triol; and
40) (2S,3R,4R,5S,6R)-2-(7-(4-chlorobenzyl)-2,3-dihydro-1H-inden-5-yl)-6-(hydroxymethyl)tetrahydro-2H-pyran-3,4,5-triol.

10. A pharmaceutical composition comprising the compound of claim 1 as an active ingredient.

11. A method of treating a disease or condition mediated by hyperglycemia in a mammal, comprising administering the compound of claim 1 to the mammal.

12. The method of claim 11, wherein the disease or condition mediated by hyperglycemia is selected from the group consisting of diabetes, a diabetes-related disease, and diabetic complications.

13. The method of claim 12, wherein the diabetes-related disease is selected from the group consisting of obesity, hyperinsulinemia, an impaired glucose metabolism, hyperlipidemia, hypercholesteremia, hypertriglyceridemia, an impaired lipid metabolism, hypertension, congestive heart failure, edema, hyperuricemia, and gout.

\* \* \* \* \*